(12) United States Patent
Dunaevsky et al.

(10) Patent No.: US 12,070,625 B2
(45) Date of Patent: Aug. 27, 2024

(54) SYSTEMS, DEVICES, AND METHODS FOR HIGH QUALITY ION BEAM FORMATION

(71) Applicant: TAE TECHNOLOGIES, INC., Foothill Ranch, CA (US)

(72) Inventors: Alexander Dunaevsky, Corona, CA (US); Artem N. Smirnov, Mission Viejo, CA (US); Alexandr A. Ivanov, Novosibirsk (RU); Vladislav Vekselman, Lake Forest, CA (US)

(73) Assignee: TAE TECHNOLOGIES, INC., Foothill Ranch, CA (US)

( * ) Notice: Subject to any disclaimer, the term of this patent is extended or adjusted under 35 U.S.C. 154(b) by 0 days.

(21) Appl. No.: 17/984,954

(22) Filed: Nov. 10, 2022

(65) Prior Publication Data

US 2023/0249002 A1    Aug. 10, 2023

Related U.S. Application Data

(63) Continuation of application No. 17/006,080, filed on Aug. 28, 2020, now Pat. No. 11,524,179.
(Continued)

(51) Int. Cl.
*A61N 5/10*    (2006.01)
*H05H 5/03*    (2006.01)
*H05H 5/06*    (2006.01)

(52) U.S. Cl.
CPC .......... *A61N 5/1077* (2013.01); *A61N 5/1048* (2013.01); *H05H 5/03* (2013.01);
(Continued)

(58) Field of Classification Search
CPC ...... A61N 5/1077–1084; A61N 5/1048; A61N 2005/1085–1098; A61N 2005/1074; H05H 5/063
See application file for complete search history.

(56) References Cited

U.S. PATENT DOCUMENTS 4,661,710 A    4/1987  Verney et al.
4,782,304 A    11/1988  Aitken
(Continued)

FOREIGN PATENT DOCUMENTS

EP    2612692 A1    7/2013
JP    59-171181    6/1986
(Continued)

OTHER PUBLICATIONS

WIPO Application No. PCT/US202/048416, PCT International Search Report and Written Opinion of the International Searching Authority mailed Apr. 8, 2021.
(Continued)

*Primary Examiner* — Thaddeus B Cox
(74) *Attorney, Agent, or Firm* — ALSTON & BIRD LLP

(57) ABSTRACT

Embodiments of systems, devices, and methods relate to a beam system. An example beam system includes a charged particle source configured to generate a beam of charged particles, a pre-accelerator system configured to accelerate the beam, and an accelerator configured to accelerate the beam from the pre-accelerator system. The pre-accelerator system can cause the beam to converge as it is propagated from the source to an input aperture of the accelerator. The pre-accelerator system can further reduce or eliminate source disturbance or damage caused by backflow traveling from the accelerator toward the source.

20 Claims, 12 Drawing Sheets

Related U.S. Application Data

(60) Provisional application No. 63/044,310, filed on Jun. 25, 2020, provisional application No. 62/895,203, filed on Sep. 3, 2019, provisional application No. 62/894,220, filed on Aug. 30, 2019, provisional application No. 62/894,106, filed on Aug. 30, 2019, provisional application No. 62/894,290, filed on Aug. 30, 2019.

(52) U.S. Cl.
CPC ....... *H05H 5/063* (2013.01); *A61N 2005/109* (2013.01); *A61N 2005/1095* (2013.01)

(56) References Cited

U.S. PATENT DOCUMENTS

| | | |
|---|---|---|
| 6,403,972 B1 | 6/2002 | Cucchetti et al. |
| 8,933,421 B2 | 1/2015 | Drees et al. |
| 9,583,302 B2 | 2/2017 | Figueroa Saavedra et al. |
| 9,818,573 B2 | 11/2017 | Abs et al. |
| 10,525,285 B1 | 1/2020 | Friedman |
| 11,524,179 B2 | 12/2022 | Dunaevsky et al. |
| 2002/0180365 A1 | 12/2002 | Okamura et al. |
| 2003/0048080 A1 | 3/2003 | Amemiya et al. |
| 2003/0152186 A1 | 8/2003 | Jurczyk et al. |
| 2003/0195582 A1 | 10/2003 | Mann |
| 2006/0011866 A1 | 1/2006 | Cho |
| 2006/0102856 A1 | 5/2006 | Matsuda et al. |
| 2007/0164237 A1 | 7/2007 | Bernhardt |
| 2007/0215459 A1 | 9/2007 | Krzeminski et al. |
| 2009/0039256 A1 | 2/2009 | Fujii et al. |
| 2009/0099513 A1 | 4/2009 | Birchard |
| 2010/0059687 A1 | 3/2010 | Balakin |
| 2011/0058167 A1 | 3/2011 | Knox et al. |
| 2011/0186746 A1 | 8/2011 | Drees et al. |
| 2012/0080618 A1 | 4/2012 | Clayton et al. |
| 2012/0135650 A1 | 5/2012 | Servante et al. |
| 2013/0231517 A1 | 9/2013 | Iwamoto et al. |
| 2014/0213867 A1 | 7/2014 | Pletcher et al. |
| 2014/0296610 A1 | 10/2014 | Nishiuchi |
| 2014/0320006 A1 | 10/2014 | Abs et al. |
| 2015/0238780 A1 | 8/2015 | Nishimura et al. |
| 2016/0064186 A1 | 3/2016 | Chang et al. |
| 2016/0263402 A1 | 9/2016 | Zhang et al. |
| 2017/0062086 A1 | 3/2017 | Park, Jr. et al. |
| 2017/0135194 A1 | 5/2017 | Belchenko et al. |
| 2017/0296844 A1 | 10/2017 | Trail et al. |
| 2020/0196428 A1 | 6/2020 | Ryding et al. |
| 2021/0166832 A1 | 6/2021 | Vekselman et al. |

FOREIGN PATENT DOCUMENTS

| | | |
|---|---|---|
| JP | H08 23067 B2 | 3/1996 |
| JP | 2003-303569 | 10/2003 |
| JP | 2009-32623 A | 2/2009 |
| JP | 2010-509714 A | 3/2010 |
| JP | 2015-217207 A | 12/2015 |
| RU | 2418338 C1 | 5/2011 |
| WO | WO 2018-168713 A1 | 9/2018 |

OTHER PUBLICATIONS

WIPO Application No. PCT/US202/048443, PCT International Search Report and Written Opinion of the International Searching Authority mailed Jan. 5, 2021.

WIPO Application No. PCT/US2020/048416, PCT International Preliminary Report on Patentability of the International Searching Authority mailed Mar. 10, 2022.

WIPO Application No. PCT/US2020/048443, PCT International Preliminary Report on Patentability of the International Searching Authority mailed Mar. 10, 2022.

U.S. Appl. No. 17/006,080, Non-Final Office Action mailed Jan. 20, 2022.

U.S. Appl. No. 17/006,080, filed Aug. 28, 2020, U.S. Pat. No. 11,524,179, Issued.

U.S. Appl. No. 17/006,397, filed Aug. 28, 2020, 2021-0166832, Pending.

Dudnikov et al., "High current density negative ion source for beam line transport studies," Proceedings of the 2001 Particcle Acelerator Conference, vol. 3, pp. 2090-2092, (Jun. 2001).

Ido et al., "Development of a Heavy Ion Beam Probe for Measuring Electrostatic Potential Profile and its Fluctuation in LHD," Plasma Science and Technology, Institute of Physics Publishing, vol. 11, No. 4, pp. 460-464, (Aug. 2009).

Kasatov et al., "Proton beam of 2 MeV 1.6 mA on a tandem accelerator with vacuum insulation," Journal of Instrumentation, Institute of Physics Publishing, vol. 9, No. 12, (Dec. 2014).

Kim et al., "Progress report of the innovated KIST ion beam facility," Nuclear Instruments & Methods in Physics Reasearch, Section B: Beam Interactions with Materials and Atoms, vol. 391, pp. 57-63, (Nov. 2016).

Kobayashi et al., "Current status of the AMS System at the University of Tokyo," Nuclear Instruments and Methods in Physics Research, Section B: Beam Interations with Materials and Atoms, vol. 123, No. 1-4, pp. 107-111, (Mar. 1997).

Mori et al., "Intense Negative Heavy Ion Source with Cusp Magnetic Field," Accelerator Science andTechnology, vol. 1 of 3, pp. 345-347, (Mar. 1989).

EP 20859978.7 Extended European Search Report mailed Aug. 25, 2023.

Bungau et al. "Target Optimisation Studies for the European Spallation Source," Proceedings of IPAC'210, Kyoto, Japan, pp. 256-258, (Jun. 2010).

Hassanzadegan et al., "System Overview and Current Status of the ESS Beam Position Monitors," Proceedings of the 5th International Particle Acelerator Conference, pp. 3653-3655, (Jul. 2014).

Hassanzadegan et al., "System Overview and Design Considerations of the BPM System of the ESS Linac," Proceeding of the 2nd International Beam Instrucmentation C onference, pp. 388-391, (Dec. 2013).

Kreiner et al., "A Tandem-electrostatic-quadrupole for accelerator-based BNCT," Nuclear Instruments and Methods in Physics Research, B 261, 751-754, (Apr. 2007).

EP 20859978.7 Extended European Search Report mailed Sep. 22, 2023.

RU Application No. 2022107821, Search Report mailed Apr. 15, 2024.

U.S. Appl. No. 17/006,397, Non-Final Office Action mailed Feb. 14, 2023.

U.S. Appl. No. 17/006,397, Notice of Allowance mailed Mar. 22, 2024.

Taskaev et al., "Vacuum-Insulation Tandem Accelerator for oron Neutron Capture Theraply," Proceedings of IPAC2011, Switzerland, CERN, Sep. 2011, p. 3615-3617.

SYSTEMS, DEVICES, AND METHODS FOR HIGH QUALITY ION BEAM FORMATION

CROSS-REFERENCE TO RELATED APPLICATIONS

The present application is a continuation of U.S. application Ser. No. 17/006,080, titled "SYSTEMS, DEVICES, AND METHODS FOR HIGH QUALITY ION BEAM FORMATION," filed Aug. 28, 2020, now U.S. Pat. No. 11,524,179, which claims priority to U.S. Provisional Application Ser. No. 63/044,310, titled "SYSTEMS, DEVICES, AND METHODS FOR HIGH QUALITY ION BEAM FORMATION," filed Jun. 25, 2020, and to U.S. Provisional Application Ser. No. 62/895,203, titled "EINZEL LENS FOR LOW ENERGY ION BEAM TRANSPORT," filed Sep. 3, 2019, and to U.S. Provisional Application Ser. No. 62/894,106, titled "NEUTRON GENERATING TARGET FOR NEUTRON BEAM SYSTEMS," filed Aug. 30, 2019, and to U.S. Provisional Application Ser. No. 62/894,220, titled "SYSTEMS AND METHODS FOR GAS PUFF BEAM IMAGING," filed Aug. 30, 2019, and to U.S. Provisional Application Ser. No. 62/894,290, titled "SYSTEMS AND METHODS FOR FAST BEAM POSITION MONITORING," filed Aug. 30, 2019, all of which are incorporated herein by reference in their entirety for all purposes.

FIELD

The subject matter described herein relates generally to systems, devices, and methods of forming high-quality ion beams for tandem accelerator systems.

BACKGROUND

Boron neutron capture therapy (BNCT) is a modality of treatment of a variety of types of cancer, including some of the most difficult types. BNCT is a technique that selectively aims to treat tumor cells while sparing the normal cells using a boron compound. A substance that contains boron is injected into a blood vessel, and the boron collects in tumor cells. The patient then receives radiation therapy with neutrons (e.g., in the form of a neutron beam). The neutrons react with the boron to kill the tumor cells while reducing harm to surrounding normal cells. Prolonged clinical research has proven that a beam of neutrons with an energy spectrum within 3-30 kiloelectronvolts (keV) is preferable to achieve a more efficient cancer treatment while decreasing a radiation load on a patient. This energy spectrum or range is frequently referred to as epithermal.

Most conventional methods for the generation of epithermal neutrons (e.g., epithermal neutron beams) are based on nuclear reactions of protons with either beryllium or lithium (e.g., a beryllium target or a lithium target). In both cases, the energy spectrum of the resulting neutrons is shifted to higher energies and therefore requires moderation. Such slowing of the neutrons down to the required energies (e.g., within the epithermal spectrum), together with forming the requisite neutron beam for BNCT, is conventionally achieved using beam shaping assemblies (BSA).

A cyclotron accelerator accelerates charged particles outwards from a center of the accelerator along a spiral path. The particles are held to a spiral trajectory by a static magnetic field and accelerated by a rapidly varying (radio frequency) electric field. The reaction of protons with a beryllium target is characterized by a high yield of neutrons, which enables maintaining of a relatively low proton beam current, for example, within limits achievable on cyclotron accelerators of protons. The energy of the proton beam is also within the limits of cyclotron accelerators. Accordingly, neutron sources based on cyclotron accelerators and beryllium targets are characterized by high neutron yield. However, the energy spectrum of the resulting neutrons is shifted towards higher energies and, as described above, requires substantial moderation in complicated BSAs. Such complicated BSAs are inefficient for slowing the neutrons and forming the requisite neutron beam for ideal BNCT applications.

High energy accelerators are usually expensive, and protons and neutrons with higher energies cause higher activation of system components, which makes systems with beryllium targets less attractive for BNCT treatment centers.

Beams of epithermal neutrons formed in cyclotron-based systems with beryllium targets have flux densities comparable with systems with lithium targets. However, systems with lithium targets result in lower energies of the proton beam, usually within the range of 1.9-3.0 Megaelectronvolts (MeV). Existing proton beam accelerators designed for lithium targets can be divided in two categories: RF-based accelerators and Electrostatic accelerators.

RF-based accelerators: Typically, RF-based proton accelerators for the present requisite energy range are based on Radio Frequency Quadrupoles, or RFQs. An RFQ is a linear accelerator which focuses and accelerates a continuous beam of charged particles with high efficiency while preserving emittance. The focusing as well as the acceleration are performed by a radio frequency (RF) electric field. While RFQ technology is mature, it remains still expensive and unattractively complex for manufacturing and operation. Moreover, it is difficult to build an RFQ system for an average current of 10 milliamps (mA) or higher.

Electrostatic accelerators: The present requisite energy range is within reach for electrostatic accelerators. Electrostatic accelerators accelerate charged particles by subjecting them to a static high voltage potential. For example, a high voltage terminal is kept as a static potential on the order of millions of volts (e.g., also referred to as an accelerating voltage). Electrostatic accelerators are usually substantially less expensive, more compact, and more energy efficient than other conventional solutions. Electrostatic accelerators also advantageously provide the ability to adjust the spectrum of the resulting neutrons by variation of the proton beam energy.

Generation of requisite accelerating voltages higher than 2 Megavolts (MV) in electrostatic accelerator systems with direct acceleration is highly challenging, which limits the achievable energy of the ideal proton beam. Placement of a proton source at a high voltage end of the electrostatic accelerator limits the ability to form the injected proton beam with low emittance, which limits the quality of the accelerated beam. Control and maintenance of the proton injector/source at the high voltage end of the electrostatic accelerator is also very technically challenging.

A tandem accelerator is a type of electrostatic accelerator that can employ a two-step acceleration of ion particles using a single high voltage terminal. The high voltage is used to form, for example, an increasingly positive gradient that is applied to the incoming negative beam to accelerate it, at which point the tandem accelerator converts the negative beam to a positive beam, and then the high voltage is used again to form a reversed decreasingly positive gradient that accelerates (e.g., pushes) the positive beam from the tandem accelerator. Because the high voltage can be used twice, generation of proton beams with a particle energy of 3 MeV typically requires an accelerating voltage of only 1.5 MV, which is within the reach of modern technologies of electrical insulation. Moreover, an ion source of a tandem accelerator is placed at the ground potential, which maintaining and control of the ion source easier.

In ion beam systems utilizing plasma-based ion sources, ions are extracted from a boundary surface (called a meniscus) of the plasma. The shape and parameters of the boundary surface are characterized by the strong dependence on the extracted current density, local rates of ionization, recombination and diffusion, and applied electric field distribution. A newborn ion beam is typically highly divergent, aberrant (an effect of the magnetic dipole separating electrons and ions of the same polarity) and subjected to space charge effects due to low initial energy. As a result, various existing solutions face several drawbacks.

Single aperture sources of negative hydrogen ions with sufficiently high current usually face a number of challenges, such as high initial beam divergence due to conditions of high current beam generation; limited beam acceleration in the ion source apertures due to the high gas load required for high current beam generation; and beam divergence due to the space charge of the beam, which is more pronounced at lower energies of the beam particles.

For these and other reasons, a need exists for improved, efficient, and compact systems, devices, and methods that provide high-quality ion beams for tandem accelerator systems.

SUMMARY

Example embodiments of systems, devices, and methods are described herein for forming high-quality ion beams that can be used in various accelerator systems. Embodiments of the present disclosure are directed to beam systems, the devices therein, and their methods of use. An example beam system includes a particle source (e.g., an ion source) configured to generate particles in a beam form, a pre-accelerator system configured to accelerate the particles from the source, and an accelerator configured to accelerate the particle from the pre-accelerator system. The pre-accelerator system can cause the beam to converge as it is propagated from the source to an input aperture of the accelerator. The pre-accelerator system can further reduce or eliminate source disturbance or damage caused by backflow traveling from the accelerator toward the source.

Other systems, devices, methods, features and advantages of the subject matter described herein will be or will become apparent to one with skill in the art upon examination of the following figures and detailed description. It is intended that all such additional systems, methods, features and advantages be included within this description, be within the scope of the subject matter described herein and be protected by the accompanying claims. In no way should the features of the example embodiments be construed as limiting the appended claims, absent express recitation of those features in the claims.

BRIEF DESCRIPTION OF FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

The term "particle" is used broadly herein and, unless otherwise limited, can be used to describe an electron, a proton (or H+ ion), or a neutral, as well as a species having more than one electron, proton, and/or neutron (e.g., other ions, atoms, and molecules).

The aforementioned and other limitations resulting in high beam divergence and low beam energy make it difficult to design an ion injector suitable for operation with particle accelerators. Taking a tandem accelerator as an example, low energies of the negative ions (e.g., H− ions) injected into the tandem accelerator can create unfavorable conditions in the first accelerating gap of the tandem accelerator. Indeed, output energies of negative ion sources are usually limited by 20-40 keV. When such negative ions are injected into the first acceleration gap of the tandem accelerator, which usually has an accelerating voltage of about 200 kilovolts (kV), the negative ions typically reach an energy of about 100 keV in the middle of the first acceleration gap.

Figure 5:
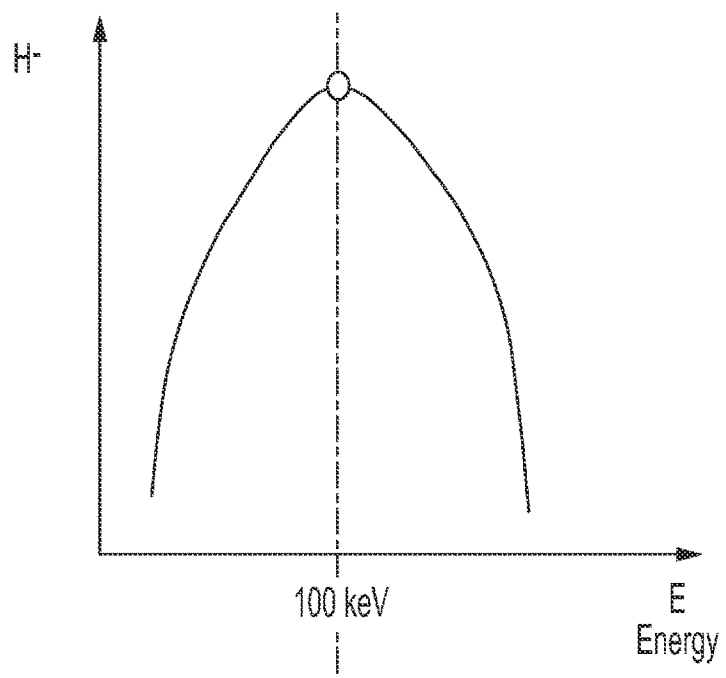
FIG. 5 illustrates a cross-section of an example ionization curve.

The energy of 100 keV corresponds to the approximate maximum of the ionization cross section for negative hydrogen ions (e.g., as shown in FIG. 5). The ionization cross section represents a measure of how large a particular particle appears to other particles while moving through space. Accelerators can often have trace amounts of background gas present in the near vacuum environment. For tandem accelerators, background gas (e.g., argon neutrals) can be purposefully introduced by a gaseous charge exchange device that is used to modify the charge of the incoming beam in the center of the tandem accelerator. The beam particles, such as H– ions, can ionize this background gas, and this ionization can be substantial or intense. In such tandem accelerators with gaseous charge exchange targets, the resulting relative high pressure of the background gas, and a larger ionization cross section, can mean that an H– ion is more likely to collide with background gas in the first accelerating gap of the tandem accelerator.

Moreover, intense ionization in the first acceleration gap of a tandem accelerator induces beam-sustained plasma discharges in the first acceleration gap, which lead to several drawbacks, including: (i) high voltage breakdown of the tandem accelerator, which makes the accelerator inoperable for an undesirable duration of time (e.g., hundreds of seconds); (ii) overload of the high voltage power supply, which leads to decreased voltage on the first acceleration gap and, as a result, defocusing of the beam and a decrease in the beam energy; (iii) overheating of the electrodes of the tandem accelerator; (iv) formation of intense backflow of accelerated positive ions, which overheat and disturb operation of the particle source; and (v) generation of bremsstrahlung radiation, which irradiates surfaces of the high voltage insulators of the tandem accelerator and decrease their high voltage strength. Bremsstrahlung radiation is radiation given off by a charged particle due to its acceleration caused by an electric field of another charged particle.

Figure 7:
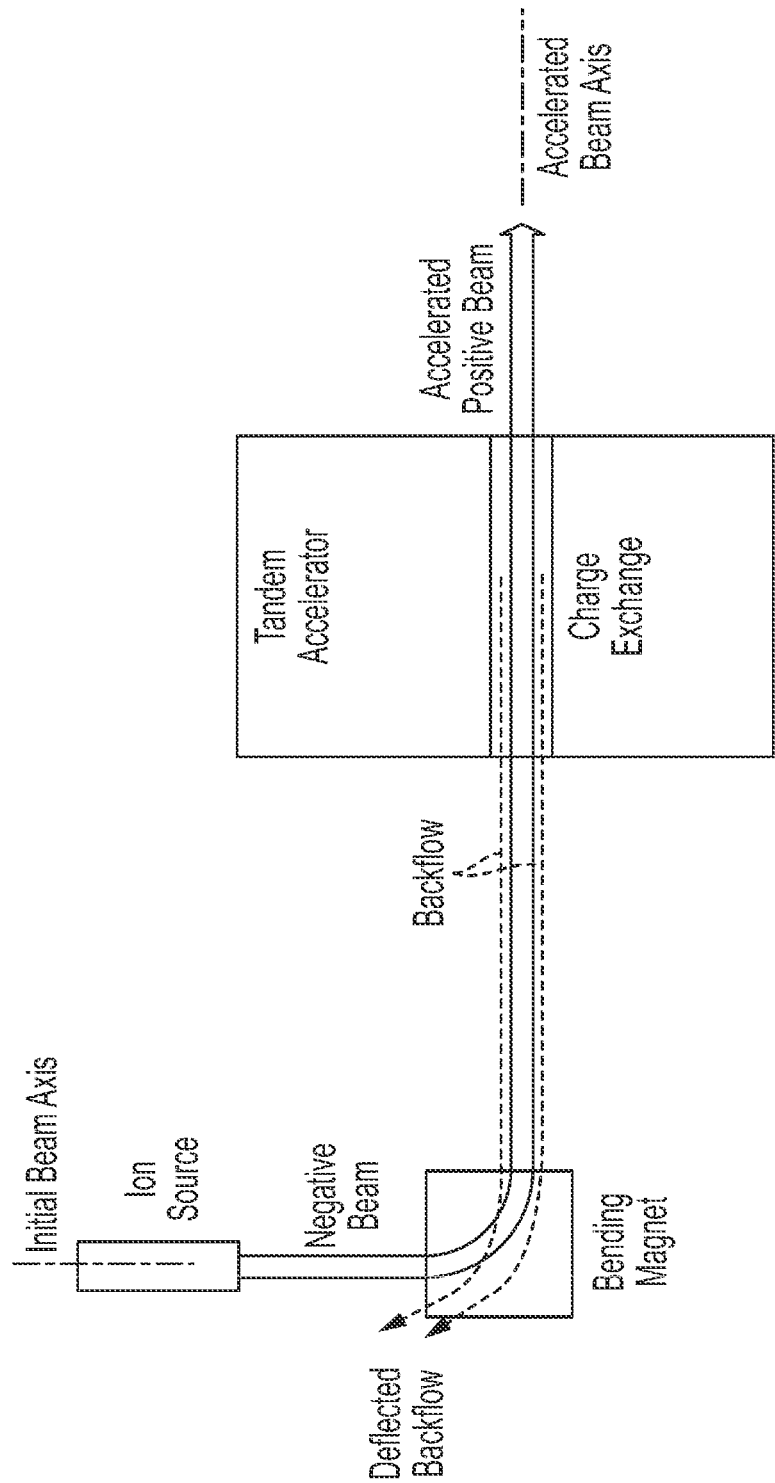
FIG. 7 illustrates an example beam injector system employing a vertical ion source and bending magnets.

High current of the negative ion beam may also require substantial efforts to focus the negative ion beam on the input aperture of the tandem accelerator. Usually, injectors of the negative ion beams with currents higher than 5 milliamps (mA) are complex and have a number of focusing magnetic elements and a gas- or plasma-filled beamline to compensate for the space charge of the ion beam. In such an example as depicted in FIG. 7, an injector of negative ion beams includes a vertical ion source and utilizes a bending magnet to focus a resulting ion beam toward an input aperture. Such systems suffer from drawbacks including low beam quality and an elliptical beam. An elliptical beam is undesirable for a tandem accelerator, thus such implementations require significantly complex beam handling to achieve a beam quality (e.g., substantially non-elliptical or substantially circular cross section) for the tandem accelerator. Moreover, any accelerator having gas filled beamlines, even in a near vacuum environment, can suffer from substantial losses of beam current due to charge exchange.

Example embodiments of systems, devices, and methods are described herein for a pre-accelerator system for use with a particle accelerator. Particle accelerators are a common example, and the embodiments described herein can be used with any type of particle accelerator or in any particle accelerator application involving production of a charged particle beam at specified energies for supply to the particle accelerator. Embodiments of the present pre-accelerator system or ion beam injector are suited to provide a negative particle beam to a tandem accelerator, but this is just an example type of accelerator. The pre-accelerator embodiments described herein can be implemented in: particle accelerators used as scientific tools, such as for nuclear physics research; particle accelerators used in industrial or manufacturing processes, such as the manufacturing of semiconductor chips; accelerators for the alteration of material properties (such as surface treatment); particle accelerators for the irradiation of food; and particle accelerators for pathogen destruction in medical sterilization. The embodiments can also be used in imaging applications, such as cargo or container inspection. And by way of another non-exhaustive example, the embodiments can be used in particle accelerators for medical applications, such as medical diagnostic systems, medical imaging systems, or radiation therapy systems.

One such radiation therapy system is a BNCT system. For ease of description, many embodiments described herein will be done so in the context of a neutron beam system for use in BNCT, although the embodiments are not limited to just neutron beams nor BNCT applications. Embodiments of the present disclosure enable configuration of an accelerator system (also referred to herein as a pre-accelerator system) for generating a proton beam with parameters suitable for sources of neutrons for BNCT with neutron generating targets, such as lithium (Li) or beryllium (Be).

For efficient generation of epithermal neutrons on a lithium target, a beam of protons with energies of 1.9-3.0 MeV is desirable. The formation of a neutron beam with a preferable flux density for reasonably short treatment time, in such applications, may also involve a proton beam current above 5 mA. In order to employ tandem accelerator systems in such applications, a source of negative ions of hydrogen may be preferred. Sources of negative hydrogen ions with sufficiently high current can have high emittance, which can make building a negative ion beam injector for a tandem accelerator while maintaining suitable beam quality difficult. The proposed configuration overcomes this and other difficulties and provides a compact, efficient negative ion beam source (e.g., of negative hydrogen ions) with high beam quality.

Embodiments of the present disclosure can increase the energy of charged particles right after their injection from a charged particle source, such as an ion source, which leads to a decrease in effects of the space charge. Divergence of the ion beam particles due to their space charge decreases with the increase of the particle energies, which eliminates or reduces the necessity of the gas- or plasma-filled beamlines.

Embodiments of the present disclosure can enable a short focal distance, which makes the present pre-accelerator or ion beam injector systems relatively more compact than conventional systems. Embodiments of the present disclosure can further diminish backflow, to the extent that the need to move the ion injector off of the beam axis of the accelerator (and thus to the extent a beam bending magnet is included upstream of the accelerator to substantially reorient the injected ion beam on the proper axis) is eliminated (e.g., see discussion with respect to FIG. 5). Note that use of the terms "upstream" and "downstream" refer to the direction of travel of the beam, not the direction of the backflow.

Embodiments of the present disclosure relate to using a pre-accelerator tube with dimensions selected such that a focal length of 500-1500 millimeters (mm) is achieved at the accelerating voltages of 60-180 kV. Therefore, fine tuning a beam focal spot to the location of the input aperture of the tandem accelerator may be achieved by positioning a single additional magnetic element (e.g., a solenoid) downstream from the pre-accelerator tube.

Embodiments of the present disclosure enable a decreased size of a negative ion beam at the input aperture of the tandem accelerator. Indeed, the smaller the input size of the beam, the smaller its size at the center of the tandem accelerator. A smaller radius of the beam at the center of the tandem accelerator enables a decrease in an inner diameter of the charge exchange device, which leads to a decrease in the gas flow needed to create sufficiently high gas pressure in the charge exchange device for efficient charge transformation of the beam particles. Usually, efficiency of 90-95% is considered acceptable for gas charge exchange devices. Lower gas flow decreases the background pressure in the tandem accelerator and, as a result, increases its reliability.

Compared to conventional approaches, embodiments of the present disclosure can provide the following additional benefits, among others: higher reliability of the tandem accelerator due to less probable high voltage breakdowns; higher high voltage strength of the insulators in the tandem accelerator; lower load on the first accelerating gap, resulting in more uniform and stable acceleration rate in the tandem accelerator; lower or depressed backflow from the tandem accelerator to the negative ion source; decreased generation of bremsstrahlung radiation in the first accelerating gap; and lower heat load on electrodes of the tandem accelerator.

Features of the embodiments of the present pre-accelerator system solve a number of issues related to physics of, e.g., the negative ion source and the tandem accelerator.

Embodiments of the present disclosure may be useful for any type of electrostatic accelerators of negative ions with the beam current above a few milliamps. The embodiments disclosed herein may have any additional elements including ion optics and beam diagnostics before, within, or after the pre-accelerator system, as required by a particular application.

Embodiments of the present disclosure can be used for a neutron beam system (NBS) that provides a continuous or modulated proton beam. The proton beam can have a wide range of energies and currents. For example, in some embodiments the proton beam has a particle energy in the range of 1.9-3.0 MeV with a beam current of 5-15 mA. In other embodiments, the proton beam has energies and/or currents outside these ranges. The beam can be directed to a lithium target to generate a neutron beam, or the NBS can be used with targets having other materials for neutron generation, such as beryllium instead of lithium.

In some embodiments, the ion source generates a beam of negative ions of hydrogen with a current up to 15 mA. The beam particles can be accelerated in the ion source to an energy of 30 keV (or higher). The ion source can be connected to the pre-accelerator system (with one or more intervening components), which provides additional acceleration of negative ion beam particles to the energy of 120-150 keV (or higher). The beam can be also focused in the pre-accelerator system with a focal length correspondent to the distance to the input aperture of the tandem accelerator input chamber, e.g., a distance of less than one meter (m). The pre-accelerator system can include an electrostatic lens (e.g., an einzel lens), a pre-accelerator device (e.g., a pre-accelerator tube having multiple terminals), and/or a magnetic element (e.g., one or more solenoids) for accelerating the ion beam to higher energies prior to entering the tandem accelerator.

The electrostatic lens of the pre-accelerator system can be positioned between the ion source and the pre-accelerator tube such that the electrostatic lens is downstream from a ground lens of the ion source. The electrostatic lens can reduce divergence of the ion beam from the ion source, and can also divert and collect ionized backflow particles.

The magnetic element (or magnetic focusing device) of the pre-accelerator system can be positioned between the pre-accelerator tube and the tandem accelerator, and can fine tune the beam toward the focal spot. The magnetic element can be, for example, a solenoid.

The ion beam injection scheme disclosed herein can enable operation with significant reductions in charged particle backflow, or without significant charged particle (e.g., secondary ion) backflow. This enables placement of the charged particle source such that the sourced particles are emitted along the same or substantially the same axis that traverses the accelerator, along which particles passing through the accelerator are accelerated. Because the charged particle source can emit onto the same axis used by the accelerator, no significant beam deflection is required (beyond relatively minor adjustments for fine tuning alignment), and therefore beam distortions inherent to such significant deflections can be avoided. As such, the present injection scheme enables operation of the neutron beam system without a beam deflecting magnet between the charged particle source and the tandem accelerator that changes the angle of the beam from one major axis to another (e.g., 20 degrees or more).

Figure 1A:
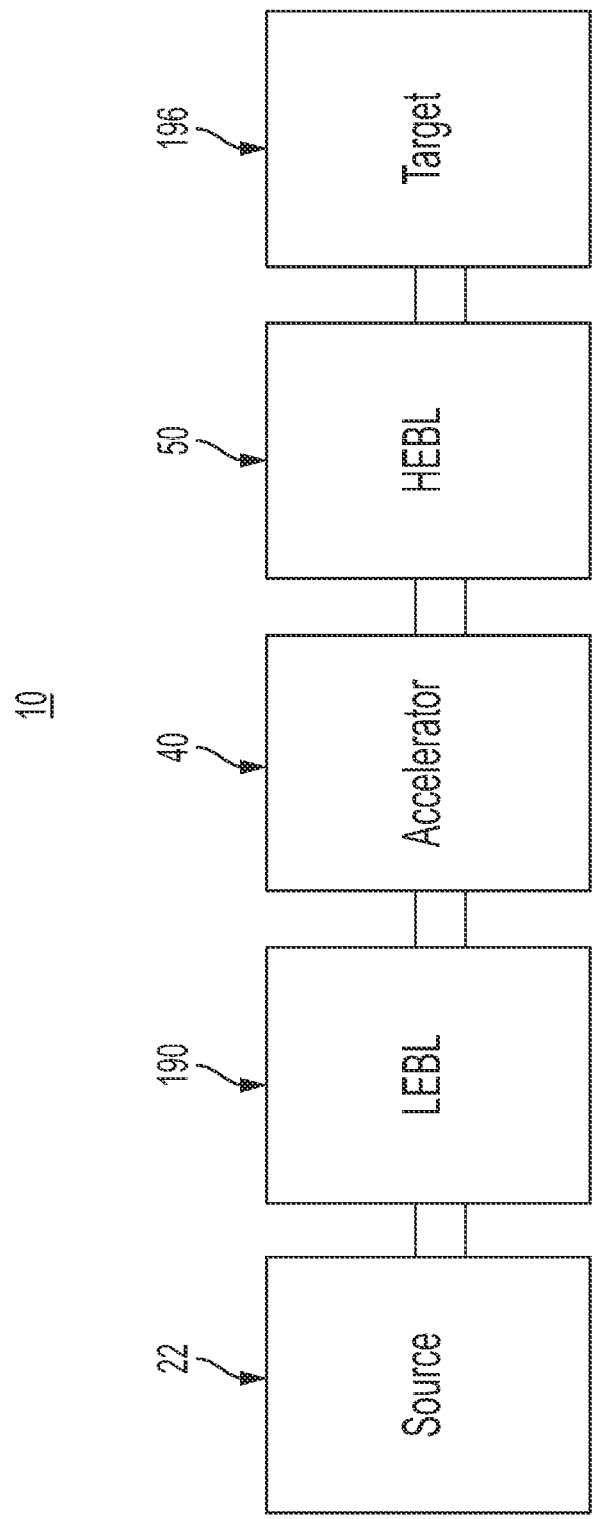
FIG. 1A is a schematic diagram of an example embodiment of a neutron beam system for use with embodiments of the present disclosure.

FIG. 1A is a schematic diagram of an example embodiment of a beam system for use with embodiments of the present disclosure. Here, beam system 10 includes a source 22, a low-energy beamline (LEBL) 190, an accelerator 40 coupled to the low-energy beamline (LEBL) 190, and a high-energy beamline (HEBL) 50 extending from accelerator 40 to a target assembly housing a target 196. LEBL 190 is configured to transport a beam from source 22 to accelerator 40, which is configured to accelerate the beam. HEBL 50 transfers the beam from an output of accelerator 40 to a target 196.

Figure 1B:
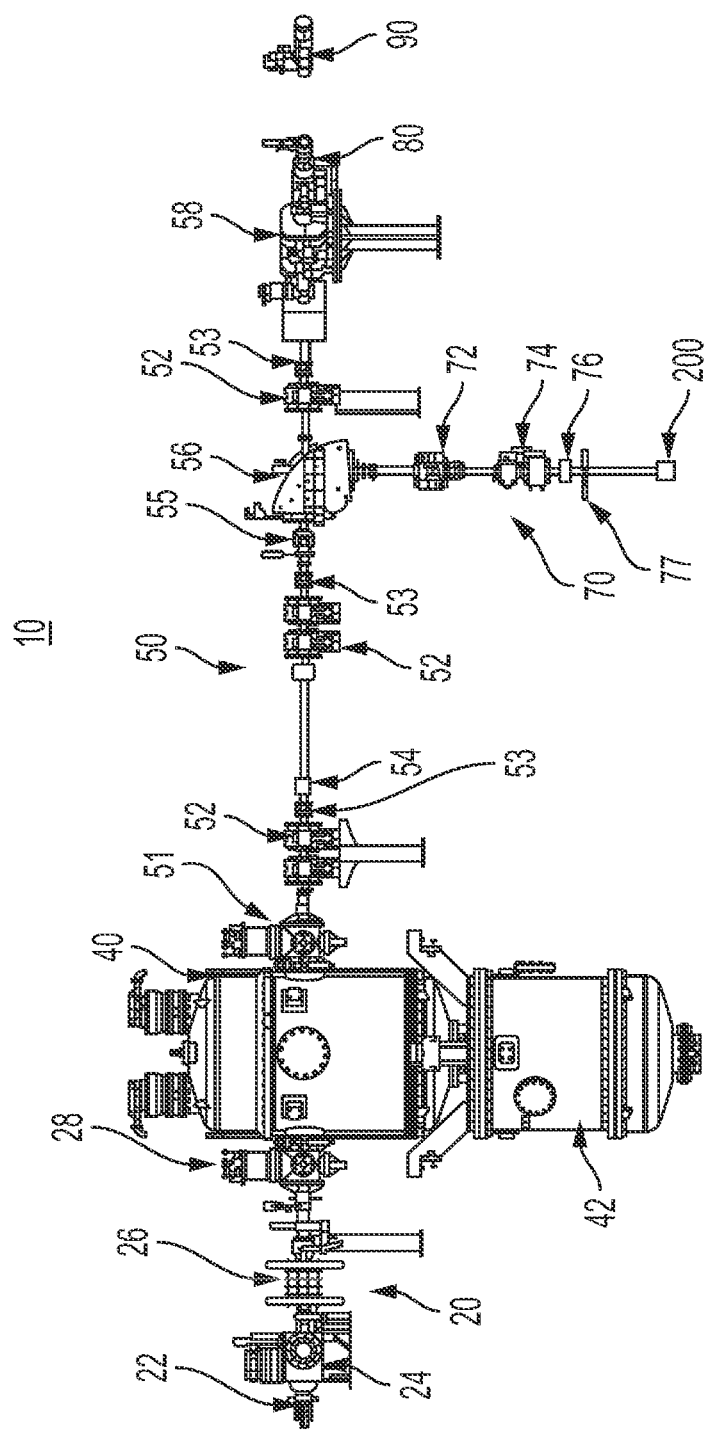
FIG. 1B is a schematic diagram of an example embodiment of a neutron beam system for use in boron neutron capture therapy (BNCT).
Figure 2:
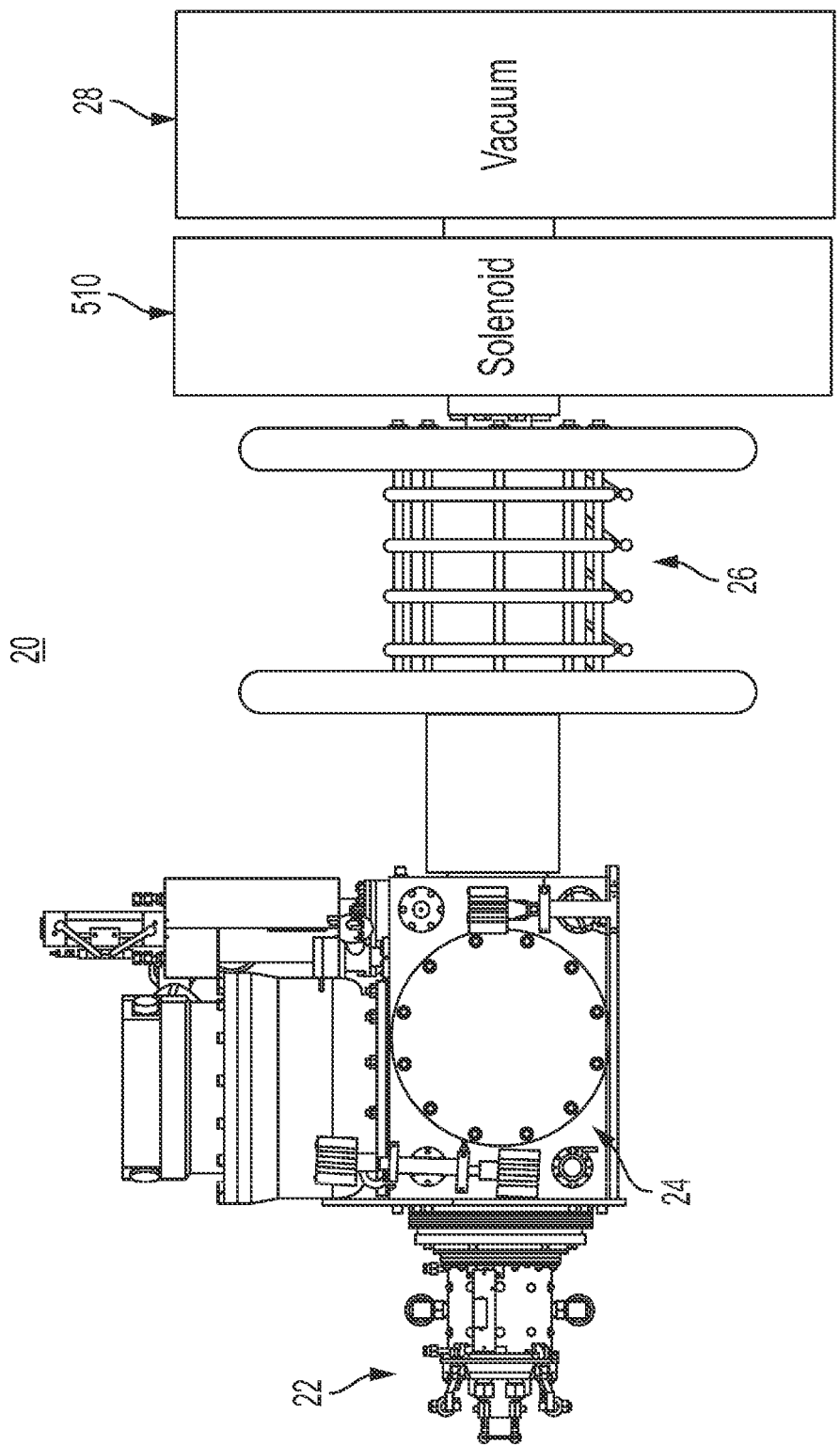
FIG. 2 illustrates an example pre-accelerator system or ion beam injector for use with embodiments of the present disclosure.

FIG. 1B is a schematic diagram illustrating an example neutron beam system 10 for use in boron neutron capture therapy (BNCT), according to embodiments of the present disclosure. The neutron beam system 10 includes a pre-accelerator system 20 forming at least a portion of the LEBL, where the pre-accelerator system 20 serves as a charged particle beam injector as shown in FIG. 2, a high voltage (HV) tandem accelerator 40 coupled to the pre-accelerator system 20, and a high-energy beamline 50 extending from the tandem accelerator 40 to a neutron target assembly 200 housing the neutron-producing target. In this embodiment beam source 22 is an ion source and the charged particle beam is a negative ion beam prior to conversion to a proton beam within tandem accelerator 40. It will be appreciated that neutron beam system 10 as well as pre-accelerator system 20 can also be used for other applications, such as cargo inspection and others, and is not limited to BNCT.

The pre-accelerator system 20 (also referred to herein as the charged particle beam injector or ion beam injector) is configured to transport the ion beam from the ion source 22 to the input (e.g., an input aperture) of the tandem accelerator 40, and thus also acts as LEBL 190.

Tandem accelerator 40, which is powered by a high voltage power supply 42 coupled thereto, can produce a proton beam with an energy generally equal to twice the voltage applied to the accelerating electrodes positioned within the tandem accelerator 40. The energy level of the proton beam can be achieved by accelerating the beam of negative hydrogen ions from the input of the tandem accelerator 40 to the innermost high-potential electrode, stripping two electrons from each ion, and then accelerating the resulting protons downstream by the same applied voltage.

The high-energy beamline 50 can transfer the proton beam from the output of the tandem accelerator 40 to the neutron-generating target in the neutron target assembly 200 positioned at the end of a branch 70 of the beamline extending into a patient treatment room. System 10 can be configured to direct the proton beam to any number of one or more targets and associated treatment areas. In this embodiment, the high-energy beamline 50 includes three branches 70, 80 and 90 to extend into three different patient treatment rooms. In this embodiment, the high-energy beamline 50 includes a pump chamber 51, quadrupole magnets 52 and 72 to prevent de-focusing of the beam, dipole or bending magnets 56 and 58 to steer the beam into treatment rooms, beam correctors 53, diagnostics such as current monitors 54 and 76, a fast beam position monitor 55 section, and a scanning magnet 74.

The design of the high-energy beamline 50 depends on the configuration of the treatment facility (e.g., a single-story configuration of a treatment facility, a two-story configuration of a treatment facility, and the like). The beam can be delivered to a target assembly (e.g., positioned near a treatment room) 200 with the use of the bending magnet 56. Quadrupole magnets 72 can be included to then focus the beam to a certain size at the target. Then, the beam passes one or more scanning magnets 74, which provides lateral movement of the beam onto the target surface in a desired pattern (e.g., spiral, curved, stepped in rows and columns, combinations thereof, and others). The beam lateral movement can help achieve smooth and even time-averaged distribution of the proton beam on the lithium target, preventing overheating and making the neutron generation as uniform as possible within the lithium layer.

After entering the scanning magnets 74, the beam can be delivered into a current monitor 76, which measures beam current. The target assembly 200 can be physically separated from the high energy beamline volume with a gate valve 77. The main function of the gate valve is separation of the vacuum volume of the beamline from the target while loading the target and/or exchanging a used target for a new one. In embodiments, the beam may not be bent by 90 degrees by a bending magnet 56, it rather goes straight to the right, then it enters the quadrupole magnets 52, which are located in the horizontal beamline. After, the beam could be bent by another bending magnet 58 to a needed angle, depending on the room configuration. Otherwise, the bending magnet 58 could be replaced with a Y-shaped magnet in order to split the beamline into two directions for two different treatment rooms located on the same floor.

FIG. 2 illustrates an example of a pre-accelerator system or ion beam injector for use with embodiments of the present disclosure. In this example, pre-accelerator system 20 includes an einzel lens 30 (not visible in FIG. 2, but depicted in FIGS. 3A-3B), a pre-accelerator tube 26, and a solenoid 510, and is configured to accelerate a negative ion beam injected from ion source 22. The pre-accelerator system 20 is configured to provide acceleration of the beam particles to the energies required for tandem accelerator 40, and to provide overall convergence of the negative ion beam to match input aperture area at an input aperture or entrance of the tandem accelerator 40. The pre-accelerator system 20 is further configured to minimize or defocus backflow as it passes from the tandem accelerator 40 through the pre-accelerator system in order to reduce the possibility of damage to ion source and/or the backflow reaching the filaments of the ion source.

In embodiments, the ion source 22 can be configured to provide a negative ion beam upstream of the einzel lens 30, and the negative ion beam continues to pass through pre-accelerator tube 26 and a magnetic focusing device (e.g., solenoid) 510. The solenoid 510 can be positioned between the pre-accelerator tube and the tandem accelerator and is electrically couplable with a power supply. The negative ion beam passes through the solenoid 510 to the tandem accelerator 40.

Pre-accelerator system 20 can also include an ion source vacuum box 24 for removing gas, and a pump chamber 28, which, with pre-accelerator tube 26 as well as the other elements described above are part of a relatively low energy beamline leading to the tandem accelerator 40. The ion source vacuum box 24, within which the einzel lens 30 can be positioned, extends from the ion source 22. The pre-accelerator tube 26 can be coupled to the ion source vacuum box 24 and to solenoid 510. A vacuum pump chamber 28 for removing gas can be coupled to the solenoid 510 and the tandem accelerator 40. The ion source 22 serves as a source of charged particles which can be accelerated, conditioned and eventually used to produce neutrons when delivered to a neutron producing target. The example embodiments will be described herein with reference to an ion source producing a negative hydrogen ion beam, although embodiments are not limited to such, and other positive or negative particles can be produced by the source.

The pre-accelerator system 20 can have zero, one, or multiple magnetic elements for purposes such as focusing and/or adjusting alignment of the beam. For example, any such magnetic elements can be used to match the beam to the beamline axis and the acceptance angle of the tandem accelerator 40. The ion vacuum box 24 may have ion optics positioned therein.

There are generally two types of negative ion sources 22, which differ by the mechanism of generation of negative ions: the surface type and the volume type. The surface type generally requires the presence of cesium (Cs) on specific internal surfaces. The volume type relies on formation of negative ions in the volume of a high current discharge plasma. While both types of ion sources can deliver the desired negative ion current for applications related to tandem accelerators, surface type negative ion sources are undesirable for modulation. That is, for modulation of a negative ion beam in embodiments described herein, negative ion sources of the volume type (e.g., without employing cesium (Cs)) are preferred.

Figure 3A:
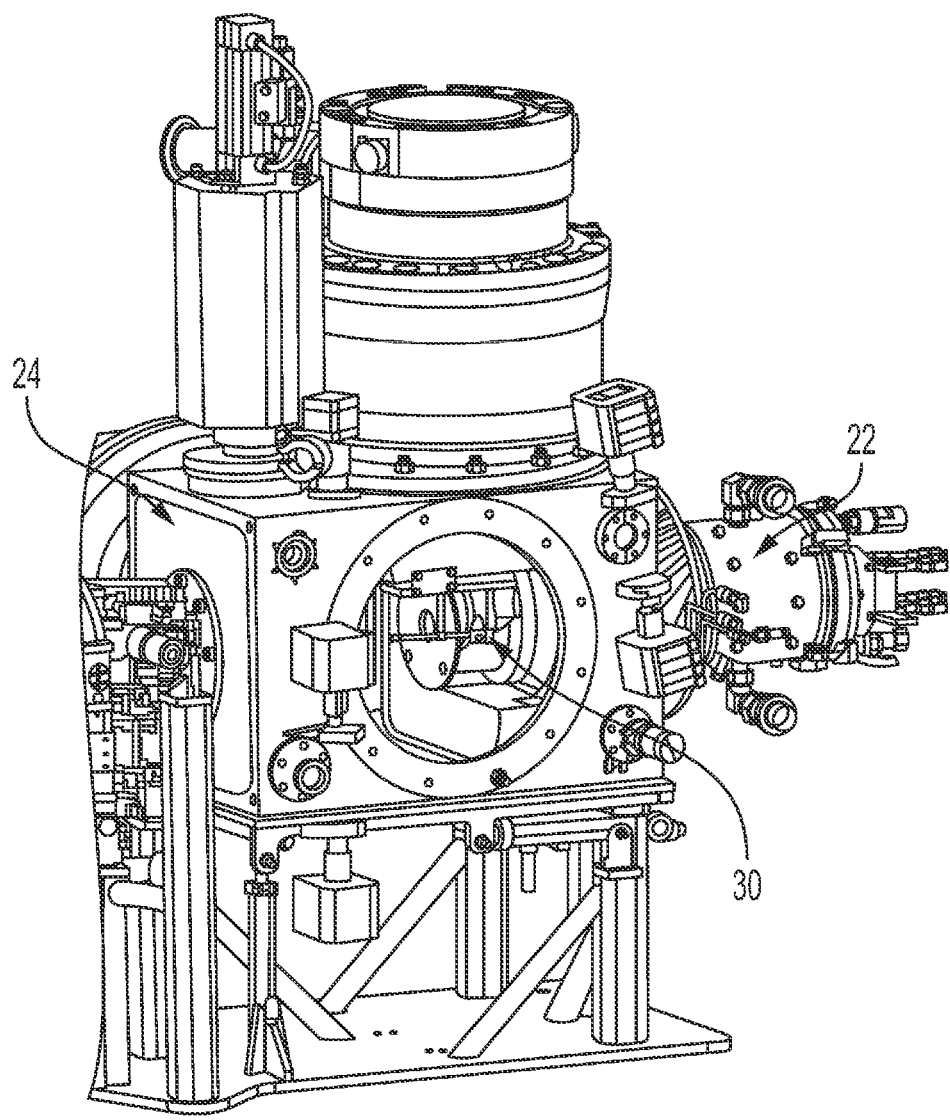
FIG. 3A is a perspective view of the ion source and the ion source vacuum box shown in FIG. 2.
Figure 3B:
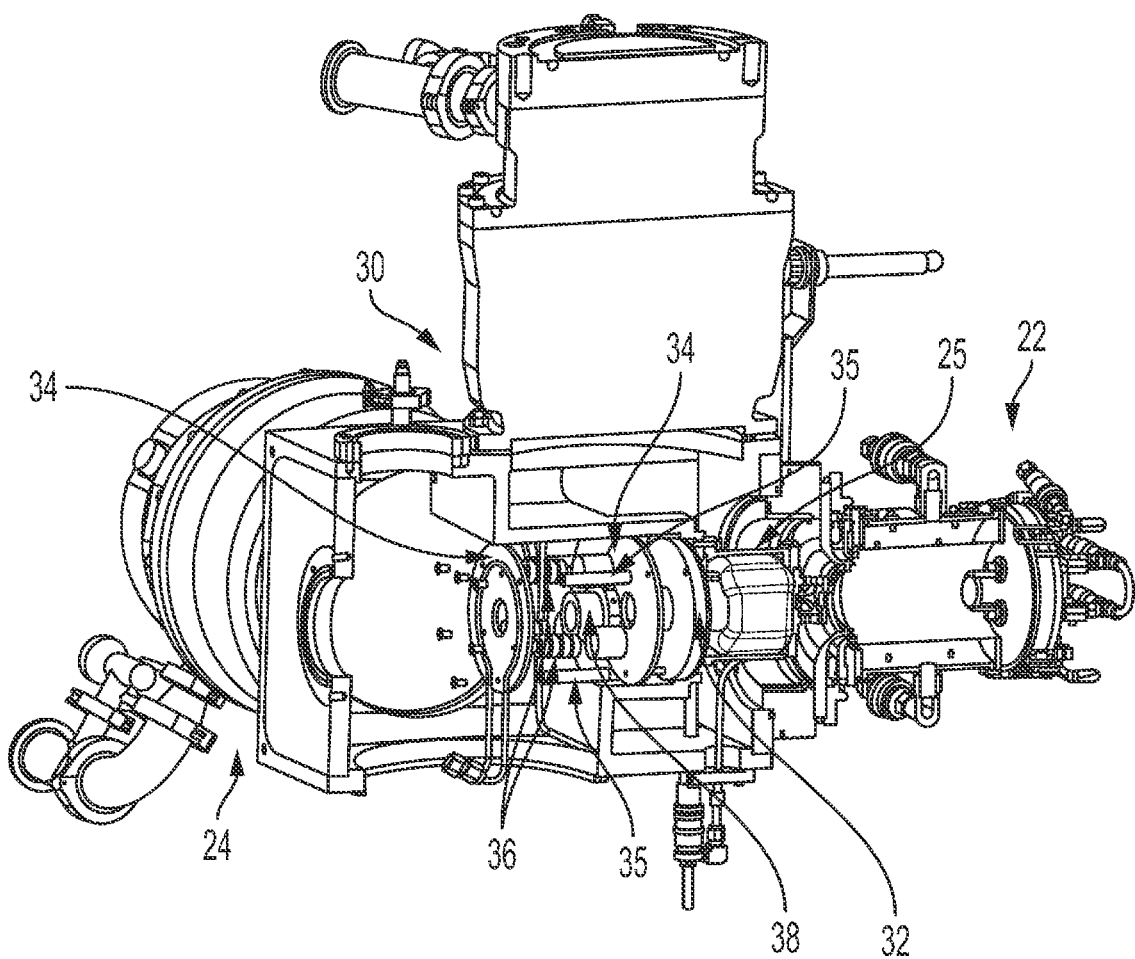
FIG. 3B is an exploded perspective view depicting an example embodiment of the einzel lens shown in FIG. 3A.

Turning to FIG. 3A, the ion source vacuum box 24 of the ion beam injector 20 can include an einzel lens 30 positioned therein. As shown in detail in FIG. 3B, the einzel lens 30, which can be mounted downstream of a ground lens 25 of the ion source 22 within the vacuum box 24, includes a mounting plate 32, two grounded electrodes 34 mounted to the mounting plate 32 and coupled to one of another in spaced relation with mounting rods 35, and a powered (biased) electrode 38 positioned between the two grounded electrodes 34. The electrodes 34 and 38 are made in the form of cylindrical apertures and assembled to have an axial axis coinciding with the beam path. The powered electrode 38 is supported by isolators (or insulators) 36 extending between the grounded electrodes or apertures 34.

The standoff isolators 36 may have a geometric design configured to inhibit development of electron avalanches and to suppress streamer formation and propagation which may result in a flashover formation. The geometric design of standoff isolators 36 may partially screen an external electric field on the insulator surface which drives the electron avalanche and effectively increases the path length. In addition, the materials of insulators/isolators 36 tend to diminish sputtering effects, loss of negative ions on surfaces, volume contamination, and formation of a conductive coating on the insulator or isolator surfaces leading to a decrease of electrical strength.

Functionally, action of the einzel lens 30 on the beam of charged particles advancing from the ion source 22 is akin to the action of optical focusing lens on a beam of light. Namely, the einzel lens 30 is focusing the incoming diverging beam into a spot at the focal plane. However, here the electric fields formed between the pairs of the powered electrode 38 and the two grounded electrodes 34 determine the focusing strength of the einzel lens (focal length distance).

By mounting the einzel lens 30 downstream of the ion source ground lens 25, it diminishes beam free space transportation where the beam is subjected to divergence due to intrinsic space charge.

The dimensions of the axisymmetric or substantially axisymmetric design of the einzel lens 30 are optimized to avoid direct interaction of extracted ions with exposed surfaces of the einzel lens 30.

In operation, negative polarity biasing of the einzel lens 30 results in higher focusing power over the positive bias polarity. Also in operation, the method of power delivery to the einzel lens 30 provides for gradual voltage growth instead of instantaneous voltage application, which reduces growth rates of electric field (dE/dt) at micro-protrusions existing on surfaces of the einzel lens 30 responsible for plasma formation via, for example, an explosive emission mechanism. Impeding of such plasma formation improves electrical strength.

Negative bias potential for an einzel lens in high background pressure is usually not possible due to electrical breakdowns. The configuration of the example embodiments of the einzel lens provided herein, enables the application of negative bias voltages sufficiently high for the 100% current utilization without electrical breakdowns.

Figure 4:
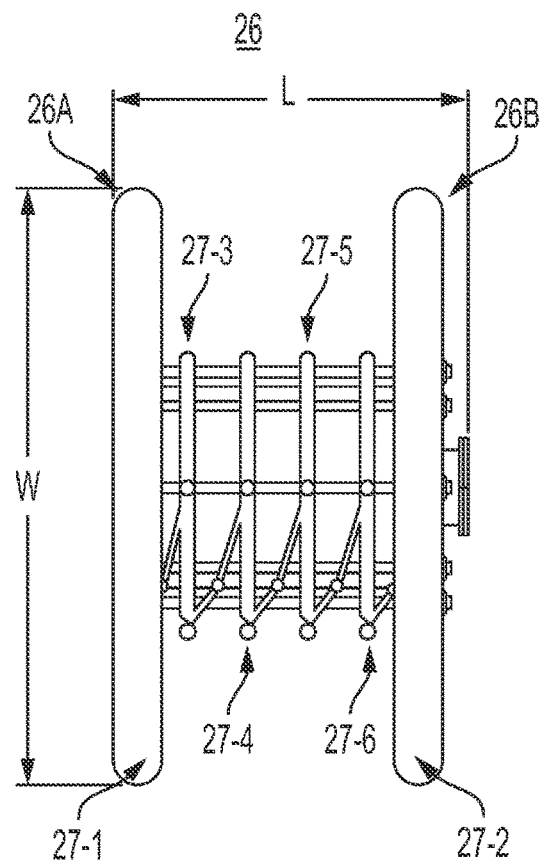
FIG. 4 illustrates an example pre-accelerator tube for use with embodiments of the present disclosure.

FIG. 4 illustrates an example pre-accelerator tube 26 for use with embodiments of the present disclosure. An example pre-accelerator tube 26 can be cylindrical in shape and includes a first pre-accelerator tube end 26A and a second pre-accelerator tube end 26B. In embodiments, the first pre-accelerator tube end 26A includes a fixture (e.g., a terminal or electrode) protruding outward from an inner cylindrical structure of the pre-accelerator tube. In embodiments, the second pre-accelerator tube end 26B includes a fixture (e.g., a terminal or electrode) protruding outward from an inner cylindrical structure of the pre-accelerator tube. That is, the fixtures protruding outward from the inner cylindrical structure of the pre-accelerator tube are cylindrical in shape but may have a larger diameter than that of the inner cylindrical structure. In embodiments, pre-accelerator tube 26 includes a plurality of pre-accelerator tube terminals 27-1, 27-2, 27-3, 27-4, 27-5, 27-6 evenly spaced from the first pre-accelerator tube end 26A to the second pre-accelerator tube end 26B. The first pre-accelerator tube end 26A may be referred to in some implementations as a proximal pre-accelerator tube end 26A in relation to the second pre-accelerator tube 26B being a distal pre-accelerator tube end 26B. Each pair of adjacent pre-accelerator tube terminals (e.g., pre-accelerator tube terminals 27-1, 27-2, 27-3, 27-4, 27-5, 27-6) may have one or more resistors connected therebetween, and the resistors can have the same (preferred) or different resistance values. In embodiments, a first terminal 27-1 at the first pre-accelerator tube end 26A is electrically couplable with a first power supply, while a second terminal 27-2 at the second pre-accelerator tube end 26B is electrically couplable with ground. Accordingly, voltage may be distributed evenly across the pre-accelerator tube 26. In embodiments, pre-accelerator tube 26 can be configured to control convergence of a negative ion beam passing therethrough such that the negative ion beam at least continues on a parallel path or continuously converges while passing through the pre-accelerator tube 26.

In embodiments, beam focusing properties of the pre-accelerator tube 26 are determined by a length and inner diameter of pre-accelerator tube 26. A combination of its length and inner diameter is selected to achieve a focal length/distance of 500-1500 mm at accelerating voltages of 60-180 kV. A length L, width W, and inner diameter of the pre-accelerator tube may vary according to a given application for which the pre-accelerator tube is used.

Figure 6:
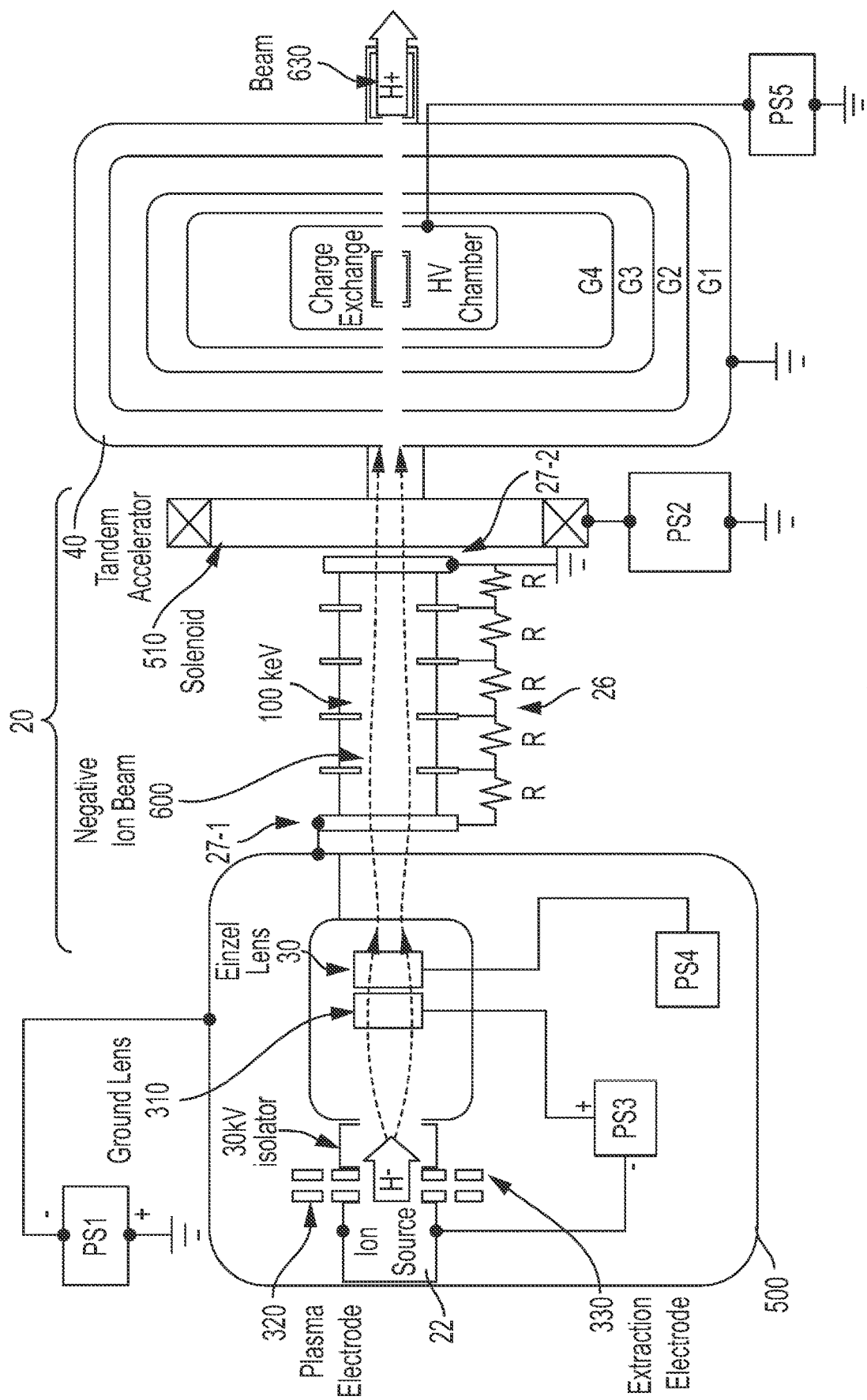
FIG. 6 illustrates operation of an example pre-accelerator system or ion beam injector, for use with embodiments of the present disclosure.

FIG. 6 illustrates beam convergence within an example pre-accelerator system, for use with embodiments of the present disclosure. An ion source 22 is optionally housed in an ion source enclosure 500. The ion source 22 includes a plurality of electrodes, such as a plasma electrode 320, a ground lens (e.g., or accelerator electrode) 310, and an extraction electrode 330. Ion source 22 is coupled with an einzel lens 30, and a negative ion beam is injected or propagated from the ion source 22 through einzel lens 30, pre-accelerator tube 26, and solenoid 510 to an input aperture of a tandem accelerator 40.

Ion source 22 can be electrically coupled, at accelerator electrode (e.g., or ground lens) 310, with a first terminal of a power supply PS3, which is in turn electrically coupled at a second terminal to an enclosure of ion source 22. Biasing of ion source 22 at accelerator electrode (e.g., or ground lens) 310 configures the pre-accelerator system 20 for maintaining and propagating a negative ion beam when such a beam is passed from the ion source 22. A plasma electrode 320 of ion source 22 can be electrically coupled to a power supply PS1 and an extraction electrode 330 of ion source 22 can be electrically coupled to a modulator (not shown) which is, in turn, electrically coupled to another power supply (not shown). Biasing of plasma electrode 320 enables ion source 22 to maintain a plasma within the ion source 22 to be used for extraction into a negative ion beam when extraction electrode 330 is biased. When extraction electrode 330 is biased, a negative ion beam is passed or propagated from ion source 22 towards tandem accelerator 40. When extraction electrode 330 is not biased, a negative ion beam is not passed or propagated from ion source 22 along to the tandem accelerator 40. Pre-accelerator tube 26 may be biased to the power supply PS1 at a first pre-accelerator tube terminal 27-1, and may be biased to ground at a second pre-accelerator tube terminal 27-2.

As discussed above, tandem accelerator 40 is powered by a high voltage power supply PS5 coupled thereto, and can produce a proton beam with an energy generally equal to twice the voltage applied to the accelerating electrodes positioned within the tandem accelerator 40. Power supply PS5 may be governed by a feedback loop (not shown) whereby voltage stability within the tandem accelerator 40 is maintained.

Figure 8:
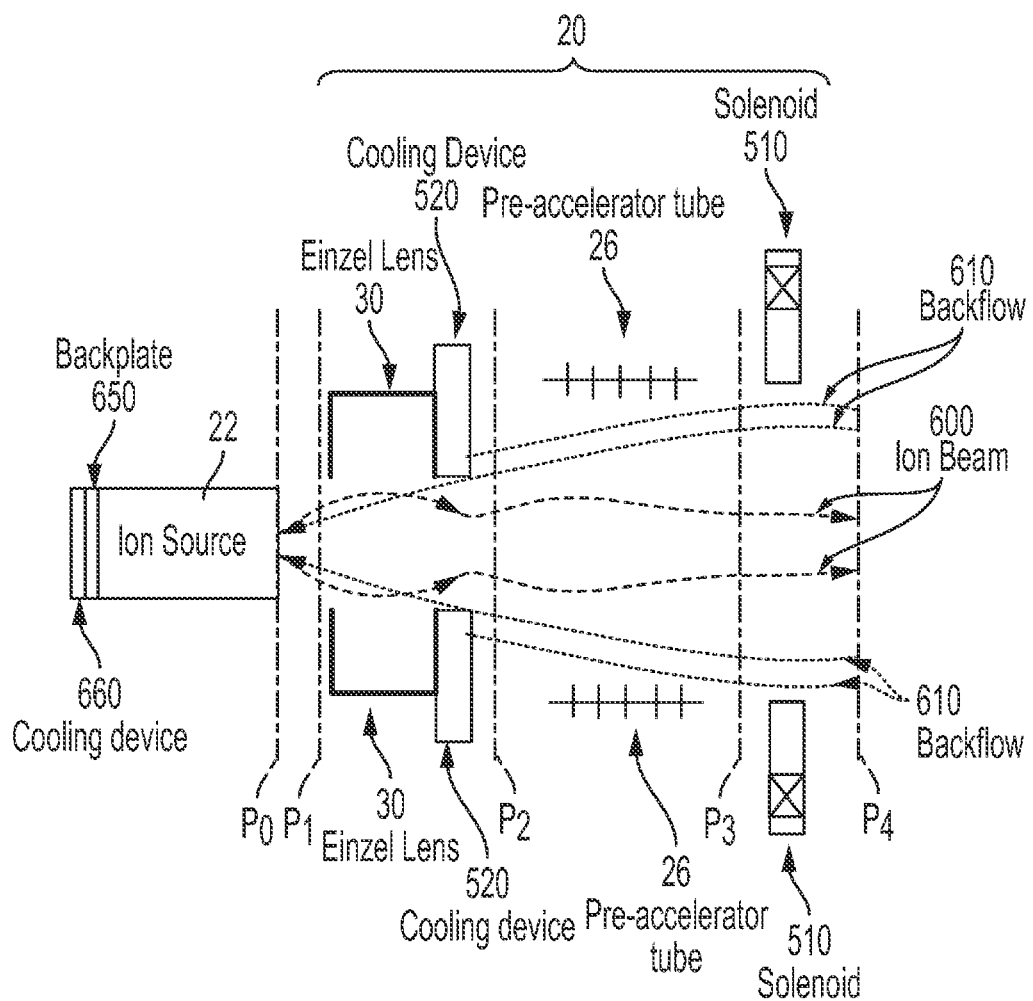
FIG. 8 further illustrates operation of an example pre-accelerator system or ion beam injector, for use with embodiments of the present disclosure.

FIG. 8 is a schematic and block diagram of an example embodiment of pre-accelerator system 20 in operation, and depicts the capability of pre-accelerator system 20 to converge negative ion beam 600. As seen here, beam 600 is divergent upon passing from ion source 22 to einzel lens 30 (as illustrated from point of travel $P_0$ to point of travel $P_1$ in FIG. 8). Einzel lens 30 is negatively biased to provide beam focusing in order to lessen the divergence of beam 600. Here, einzel lens 30 causes beam 600 to transition from a divergent form to a convergent form. Beam 600 begins to diverge again after exiting lens 30, but remains in approximately the same space constrained state between source 22 and pre-accelerator tube 26 (e.g., from point of travel $P_1$ to point of travel $P_2$ in FIG. 8). Pre-accelerator tube 26 can be configured to further provide beam focusing in order to promote convergence of negative ion beam 600 (e.g., from point of travel $P_2$ to point of travel $P_3$ in FIG. 8). Solenoid 510 can be biased in order to provide fine tuning of beam focusing to further promote convergence of negative ion beam 600 such that negative ion beam 600 is of appropriate quality and focused size when it reaches an input aperture of tandem accelerator 40 (e.g., from point of travel $P_3$ to point of travel $P_4$ in FIG. 8). Controlling the bias on solenoid 510 further allows fine tuning of beam focusing in order to ensure the beam is sufficiently and accurately aimed at the input aperture of tandem accelerator 40. Control of power supply PS1 enables coarse adjustment of a negative ion beam aimed at the input aperture of the tandem accelerator. Control of power supply PS2 enables fine tuning adjustment of the negative ion beam aimed at the input aperture.

FIG. 8 also illustrates a backflow defocusing operation of the example embodiment of pre-accelerator system 20. As discussed above, low energies of the negative ions injected into a tandem accelerator create unfavorable conditions in the first accelerating gap of the tandem accelerator. In conventional systems, when a negative ion beam is injected into the first acceleration gap (e.g., G1) of the tandem accelerator, the ions typically reach an energy of about 100 keV in the middle of the first acceleration gap.

Use of a gaseous medium (e.g., argon, nitrogen) in the charge exchange device of the tandem accelerator 40 creates the potential for the charge exchange gas to become ionized by the beam. Gaseous neutrals come from the charge exchange device in the center of the tandem accelerator when the gas is pumped into, e.g., a charge exchange tube to strip electrons from the negative ion beam (e.g., the H− ions) to create protons (e.g., H+ ions). The pressure of background gas in the tandem accelerator with a gaseous charge exchange device is often relatively high, and a larger particle cross section (e.g., 100 keV in FIG. 5) occurring in the first accelerating gap of the tandem accelerator (e.g., G1) means that a negative hydrogen ion is more likely to collide with background gas in the first accelerating gap of the tandem accelerator 40 and subsequently ionize, which can lead to deleterious effects such as arcing and breakdowns. Further, because gaseous neutrals travel from the charge exchange device in the center of the tandem accelerator back through preceding accelerating gaps (e.g., G4, G3, G2, G1) ionization of the background gas occurs in the inner gaps as well as the first accelerating gap.

In present embodiments, the ions of negative ion beam reach an energy of about 100 keV at an approximate mid-point of the pre-accelerator tube 26 (e.g., at some point between, for example, point of travel $P_2$ and point of travel $P_3$ in FIG. 8 as opposed to inside the first accelerating gap G1 of the tandem accelerator). This is because there are fewer gaseous neutrals in the middle of the pre-accelerator tube 26 due to a vacuum pump chamber (not shown) positioned between the pre-accelerator system 20 and the tandem accelerator 40, as well as the configuration of the pre-accelerator system 20. The position where the beam reaches the maximum cross-section energy of the beam's constituent particle can vary from the mid-point of the pre-accelerator tube 26, and other such positions upstream of the input aperture of the tandem accelerator are within the scope of the present subject matter (e.g., a position in proximity with end 26A or 26B of pre-accelerator tube 26, a position within solenoid 510, a position within einzel lens 30, between the aforementioned components, are examples of such).

Notwithstanding the aforementioned improvements over existing systems with respect to backflow in the first accelerating gap of a tandem accelerator, pre-accelerator system 20 may still be subject to backflow 610 passing through the system which originates from the tandem accelerator 40 to which the pre-accelerator system 26 provides a negative ion beam 600. Backflow is positive ionized gas that is accelerated by a magnetic field in the opposite direction of the accelerated beam. Gaseous neutrals traveling from the charge exchange device back through the preceding accelerating gaps (e.g., G4, G3, G2, G1) represent particles that can potentially ionize (through collisions) and become backflow. Vacuum removal of a significant amount of the gaseous neutrals coming from the tandem accelerator 40 results in a reduction of possible particles that can become backflow.

Accordingly, the components of pre-accelerator system 26 are also configured to minimize, defocus, or eliminate backflow 610 as it passes through the pre-accelerator system 26 in order to reduce the possibility of damage to ion source 22 and/or to eliminate the possibility of the backflow reaching the filaments of the ion source 22. Any biased component can defocus backflow 610, including einzel lens 30, pre-accelerator tube 26, and/or solenoid 510. For example, solenoid 510 can defocus backflow, and the amount or direction of defocus can be controlled by adjustment of the voltage applied to solenoid 510 (e.g., by second power supply PS2), which enables fine tuning of the solenoid 510 contribution toward beam focusing as well as backflow defocusing.

Similarly, adjustment of control of the biasing of pre-accelerator tube 26 and einzel lens 30 aid in de-focusing backflow 610. That is, the pre-accelerator tube 26 and einzel lens 30 may be controlled independently to reach the desired degree of focus of beam 600 and defocus of backflow 610 for minimization thereof.

Shown in FIG. 8, backflow 610 is defocused or diverted from the beam axis as it travels through solenoid 510 and pre-accelerator tube 26 (e.g., from point of travel $P_4$ to point of travel $P_2$ in FIG. 8). Backflow may be collected by any component of the beam system regardless of whether that component is biased. As shown here, some backflow is collected by cooling device 520, which is configured to cool the electrodes of einzel lens 30.

Figure 9:
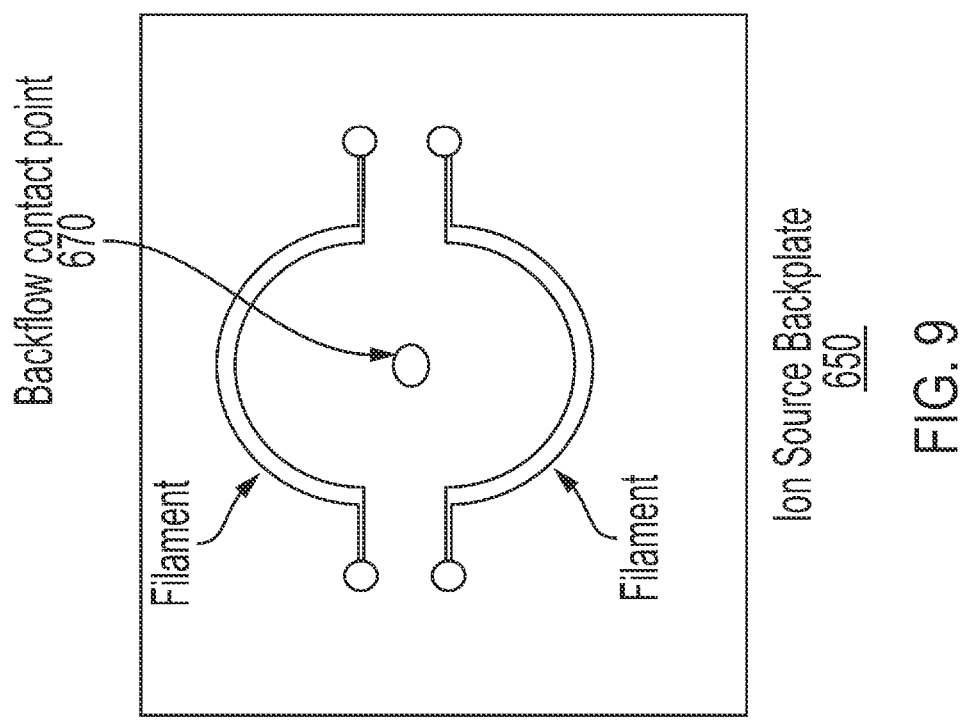
FIG. 9 illustrates an example ion source backplate for use with embodiments of the present disclosure.

Once the backflow 610 reaches the ion source 22, it is defocused such that the possibility of damage to the ion source 22 is reduced or eliminated, and cooling device 660 further reduces or eliminates backflow 610 as it reaches an upstream housing (e.g., backplate) 650 of the ion source 22. FIG. 9 illustrates an example ion source backplate assembly for use with embodiments of the present disclosure. In embodiments, backplate assembly 650 includes filaments for generating plasma to create negative hydrogen ions from the ion source 22. In embodiments, backplate assembly 650 is optionally cooled using cooling device 660 (e.g., water cooling) in order to prevent backflow 610, which may strike the backplate assembly 650 at a backflow contact point 670, from reaching the filaments. This ensures stability of the ion source 22 and eliminates reduction in reliability of the ion source 22 and pre-accelerator system 20 based upon backflow 620 from gaps within the tandem accelerator 40 and backflow 610 traveling through the pre-accelerator system 20.

Figure 10:
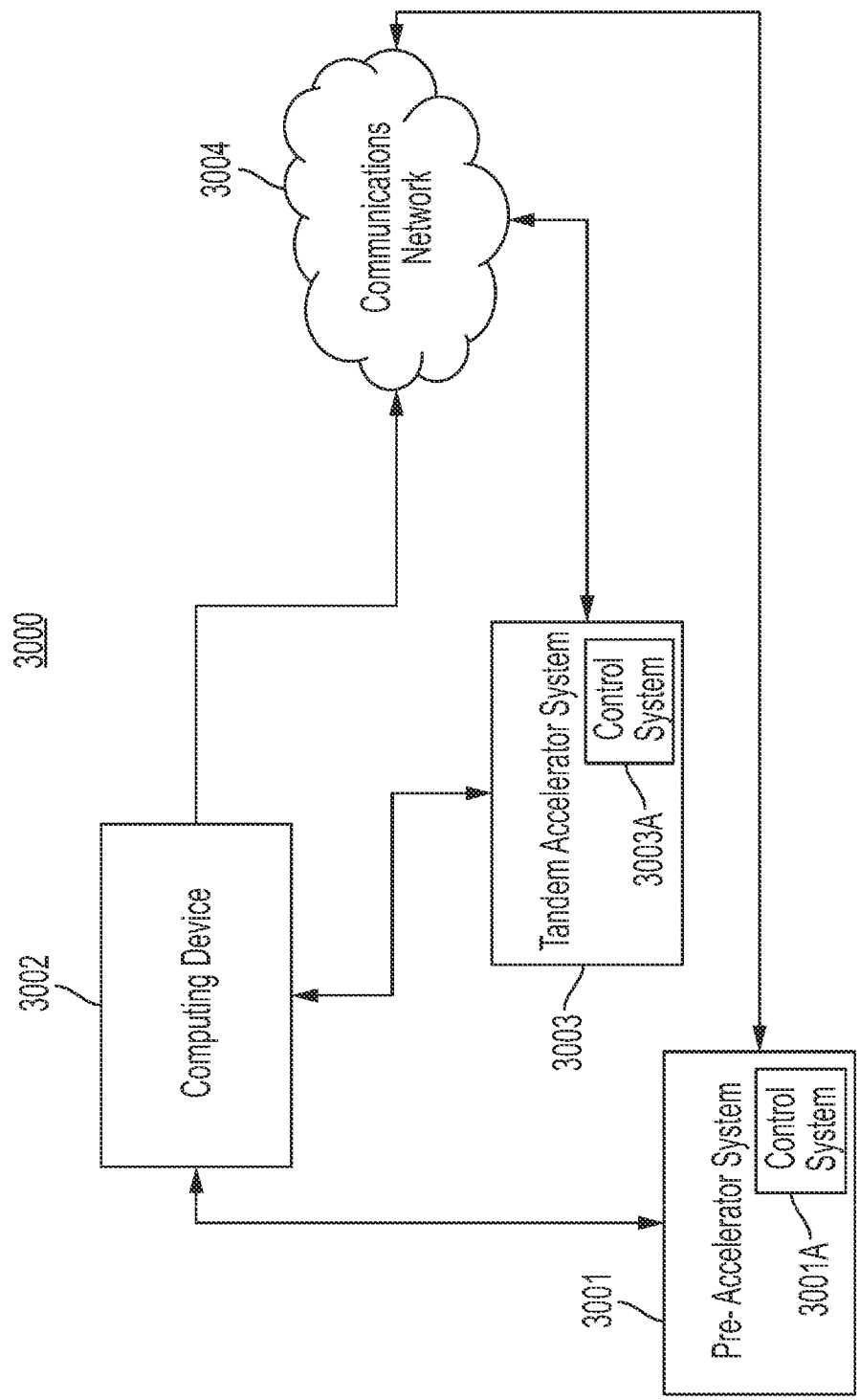
FIG. 10 illustrates a block diagram of a system within which embodiments of the present disclosure may operate.

FIG. 10 is a block diagram showing an example system 3000 within which embodiments of the present disclosure may operate. For example, the illustrated example system 3000 includes pre-accelerator system 3001, one or more computing devices 3002, and a tandem accelerator system 3003. In embodiments, pre-accelerator system 3001 and tandem accelerator system 3003 may collectively be part of an example neutron beam system (e.g., system 10 above). In such embodiments, the neutron beam system 10 may employ one or more control systems with which one or more computing devices 3002 may communicate in order to interact with the systems and components of the neutron beam system 10. Each of these devices and/or systems are configured to communicate directly with one another (not shown) or via a local network, such as network 3004.

Computing devices 3002 may be embodied by various user devices, systems, computing apparatuses, and the like. For example, a first computing device 3002 may be a desktop computer or work station associated with a particular user, while another computing device 3002 may be a laptop computer associated with a particular user, and yet another computing device 3002 may be a mobile device (e.g., a tablet or smart device). Each of the computing devices 3002 may be configured to communicate with the pre-accelerator system 3001 and/or tandem accelerator system 3003, for example through a user interface accessible via the computing device. For example, a user may execute a desktop application on the computing device 3002, which is configured to communicate with the pre-accelerator system 3001 and/or tandem accelerator system 3003.

By using a computing device 3002 to communicate with one or more of the pre-accelerator system 3001 or tandem accelerator system 3003, a user may provide operating parameters for either of the systems according to embodiments described herein. In embodiments, pre-accelerator system 3001 may include a control system 3001A by which pre-accelerator system 3001 may receive and apply operating parameters from computing device 3002. In embodiments, tandem accelerator system 3003 may include a control system 3003A by which tandem accelerator system 3003 may receive and apply operating parameters from computing device 3002.

Any of the control aspects described herein can be controlled or adjusted, managed, and/or monitored with system 3000 (e.g., computing device 3002, control system 3001A or 3003A). Examples of these control aspects include: the bias or voltage applied to any electrode of ion source 22, the bias of voltage applied to einzel lens 30, the bias or voltage applied to pre-accelerator tube 26, the bias or voltage applied to solenoid 510, the bias or voltage applied to tandem accelerator 40, the voltage output by any of the power supplies PS1-PS5, the sequence of biases or voltages applied to the components of the system for modulation, startup, or breakdown recovery, adjustment of beam position for alignment, adjustment of beam focal position, adjustment of backflow defocus amount, and others.

Communications network 3004 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, communications network 3004 may include an 802.11, 802.16, 802.20, and/or WiMax network. Further, the communications network 3004 may include a public network, such as the Internet, a private network, such as an intranet, or combinations thereof, and may utilize a variety of networking protocols now available or later developed including, but not limited to TCP/IP based networking protocols.

Figure 11:
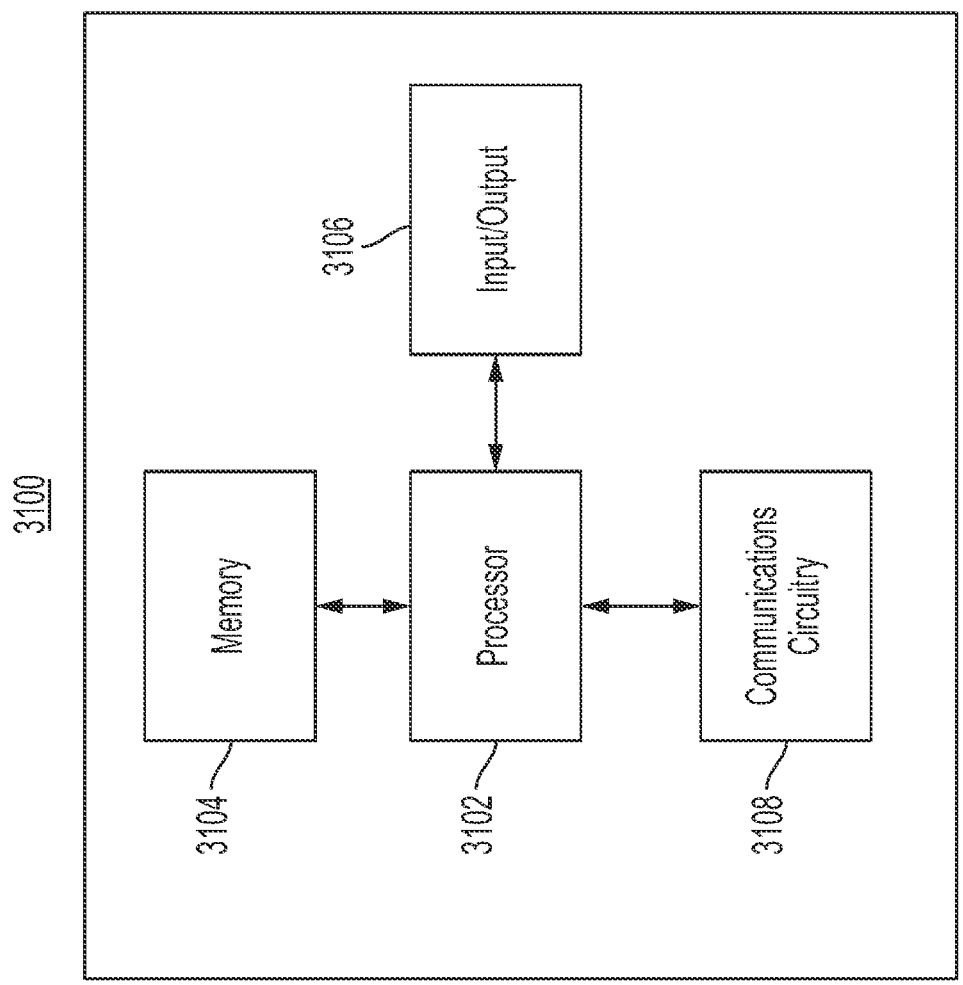
FIG. 11 illustrates an example computing apparatus that may be specially configured in accordance with embodiments of the present disclosure.

The computing device 3002 and control systems 3001A and 3003A may be embodied by one or more computing systems, such as apparatus 3100 shown in FIG. 11. As illustrated in FIG. 11, apparatus 3100 may include a processor 3102, a memory 3104, an input and/or output circuitry 3106, and communications device or circuitry 3108. These components 3102-3108 may include similar hardware. For example, two components may both leverage use of the same processor, network interface, storage medium, or the like to perform their associated functions, such that duplicate hardware is not required for each device.

The terms "device" and/or "circuitry" should be understood broadly to include hardware alone, or a combination of hardware and software (e.g., software for configuring the hardware or for accomplishing functions with the hardware). For example, in some embodiments, device and/or circuitry may include processing circuitry, storage media, network interfaces, input/output devices, and the like. In some embodiments, other elements of the apparatus 3100 may provide or supplement the functionality of particular device(s). For example, the processor 3102 may provide processing functionality, the memory 3104 may provide storage functionality, the communications device or circuitry 3108 may provide network interface functionality, and the like.

In some embodiments, processor 3102 (and/or co-processor or any other processing circuitry assisting or otherwise associated with the processor) may be in communication with memory 3104 via a bus for passing information among components of the apparatus. Memory 3104 may be non-transitory and may include, for example, one or more volatile and/or non-volatile memories. In other words, for example, memory 3104 may be an electronic storage device (e.g., a computer readable storage medium). Memory 3104 may be configured to store information, data, content, applications, instructions, or the like, for enabling the apparatus to carry out various functions in accordance with example embodiments of the present disclosure.

Processor 3102 may be embodied in a number of different ways and may, for example, include one or more processing devices configured to perform independently. Additionally or alternatively, the processor may include one or more processors configured in tandem via a bus to enable independent execution of instructions, pipelining, and/or multi-threading. The use of the terms "processing device" and/or "processing circuitry" may be understood to include a single core processor, a multi-core processor, multiple processors internal to the apparatus, and/or remote or "cloud" processors.

In an example embodiment, processor 3102 may be configured to execute instructions stored in memory 3104 or otherwise accessible to the processor. Alternatively or additionally, processor 3104 may be configured to execute hard-coded functionality. As such, whether configured by hardware or software methods, or by a combination of hardware with software, processor 3104 may represent an entity (e.g., physically embodied in circuitry) capable of performing operations according to an embodiment of the present disclosure while configured accordingly. Alternatively, as another example, when the processor is embodied as an executor of software instructions, the instructions may specifically configure the processor to perform the algorithms and/or operations described herein when the instructions are executed.

In some embodiments, apparatus 3100 may include input/output device 3106 that may, in turn, be in communication with processor 3102 to provide output to the user and, in some embodiments, to receive input from the user. Input/output device 3106 may include a user interface and may include a device display, such as a user device display, that may include a web user interface, a mobile application, a client device, or the like. In some embodiments, input/output device 3106 may also include a keyboard, a mouse, a joystick, a touch screen, touch areas, soft keys, a microphone, a speaker, or other input/output mechanisms. The processor and/or user interface circuitry including the processor may be configured to control one or more functions of one or more user interface elements through computer program instructions (e.g., software and/or firmware) stored on a memory accessible to the processor (e.g., memory 3104, and/or the like).

The communications device or circuitry 3108 may be any device or circuitry embodied in either hardware or a combination of hardware and software that is configured to receive and/or transmit data from/to a network and/or any other device or circuitry in communication with apparatus 3100. In this regard, communications device or circuitry 3108 may include, for example, a network interface for enabling communications with a wired or wireless communication network. For example, communications device or circuitry 3108 may include one or more network interface cards, antennas, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s). These signals may be transmitted by the apparatus 3100 using any of a number of wireless personal area network (PAN) technologies, such as current and future Bluetooth standards (including Bluetooth and Bluetooth Low Energy (BLE)), infrared wireless (e.g., IrDA), FREC, ultra-wideband (UWB), induction wireless transmission, or the like. In addition, it should be understood that these signals may be transmitted using Wi-Fi, Near Field Communications (NFC), Worldwide Interoperability for Microwave Access (WiMAX), or other proximity-based communications protocols.

The embodiments of devices that act on or manipulate digital information may be configured entirely as hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices. Processing circuitry for use with embodiments of the present disclosure can execute software instructions stored on memory that cause the processing circuitry to take a host of different actions and control the other components in figures herein.

Memory for use with embodiments of the present disclosure can be shared by one or more of the various functional units, or can be distributed amongst two or more of them (e.g., as separate memories present within different chips). Memory can also be a separate chip of its own. The memory is non-transitory, and can further include volatile (e.g., RAM, etc.) and/or non-volatile memory (e.g., ROM, flash memory, F-RAM, etc.).

Any such computer program instructions and/or other type of code may be loaded onto a computer, processor, or other programmable apparatus' circuitry to produce a machine, such that the computer, processor, or other programmable circuitry that executes the code on the machine creates the structure for implementing various functions, including those described herein. Computer program instructions for carrying out operations in accordance with the described subject matter may be written in any combination of one or more programming languages, including an object oriented programming language such as Java, JavaScript, Smalltalk, C++, C#, Transact-SQL, XML, PUP or the like and conventional procedural programming languages, such as the "C" programming language or similar programming languages.

Various aspects of the present subject matter are set forth below, in review of, and/or in supplementation to, the embodiments described thus far, with the emphasis here being on the interrelation and interchangeability of the following embodiments. In other words, an emphasis is on the fact that each feature of the embodiments can be combined with each and every other feature unless explicitly stated otherwise or logically implausible.

In many embodiments, a beam system includes a particle source configured to emit a charged particle beam, a pre-accelerator system configured to accelerate the charged particle beam from the particle source, and an accelerator configured to accelerate the charged particle beam from the pre-accelerator system. In some of these embodiments, the particle source is an ion source and the charged particle beam is an ion beam comprising negative hydrogen ions. In some of these embodiments, the pre-accelerator system includes at least one of: an electrostatic lens, a pre-accelerator device, or a magnetic focusing device. In some of these embodiments, the pre-accelerator system includes an electrostatic lens, a pre-accelerator device, and a magnetic focusing device.

In some of these embodiments, the electrostatic lens is an einzel lens, the pre-accelerator device is a pre-accelerator tube including a plurality of acceleration terminals, and the magnetic focusing device is a solenoid. In some of these embodiments, the electrostatic lens is downstream of the particle source, the pre-accelerator device is downstream of the electrostatic lens, and the magnetic focusing device is downstream of the pre-accelerator device. In some of these embodiments, the electrostatic lens is an einzel lens including two grounded electrodes coupled to one another in spaced relation, and a biased electrode positioned between the two grounded electrodes and supported by insulators extending therebetween. In some of these embodiments, one or more of the biased electrode or the two grounded electrodes are configured for negative biasing.

In some of these embodiments, the pre-accelerator tube includes a first pre-accelerator tube terminal and a second pre-accelerator tube terminal. In some of these embodiments, the first pre-accelerator tube terminal is electrically couplable with a first power supply. In some of these embodiments, the second pre-accelerator tube terminal is electrically couplable with ground.

In some of these embodiments, the accelerator is a tandem accelerator including a plurality of input electrodes, a charge exchange device, and a plurality of output electrodes. In some of these embodiments, the charged particle beam is a negative ion beam. In some of these embodiments, the plurality of input electrodes are configured to accelerate a negative ion beam from the pre-accelerator system, the charge exchange device is configured to convert the negative ion beam to a positive beam, and the plurality of output electrodes are configured to accelerate the positive beam.

In some of these embodiments, the beam system further includes a target device configured to form a neutral beam from the positive beam received from the tandem accelerator.

In some of these embodiments, the pre-accelerator system is positioned adjacent to and downstream from the particle source.

In some of these embodiments, the pre-accelerator device is positioned downstream from the electrostatic lens. In some of these embodiments, the magnetic focusing device is positioned downstream from the pre-accelerator device. In some of these embodiments, the pre-accelerator device is positioned downstream from one or more of the electrostatic lens or the particle source. In some of these embodiments, the magnetic focusing device is positioned downstream from one or more of an einzel lens, a pre-accelerator tube, or the particle source.

In some of these embodiments, the beam system further includes one or more vacuum pump chambers. In some of these embodiments, a first vacuum pump chamber is positioned between the pre-accelerator system and the accelerator. In some of these embodiments, a second vacuum pump chamber is positioned between the particle source and the pre-accelerator system.

In some of these embodiments, one or more vacuum pump chambers are positioned on the accelerator.

In some of these embodiments, the particle source includes a wall having one or more filaments located adjacent thereto. In some of these embodiments, the beam system includes a first cooling device configured to cool the wall. In some of these embodiments, the beam system includes a second cooling device configured to cool the einzel lens. In some of these embodiments, the first and second cooling devices are configured to use a fluid coolant.

In some of these embodiments, the pre-accelerator system is configured to cause the charged particle beam to propagate from the particle source to converge at an input aperture of the accelerator.

In some of these embodiments, the pre-accelerator system is configured to defocus and collect ionized backflow that propagates from the accelerator towards the particle source.

In some of these embodiments, the pre-accelerator system is configured to transition the particle beam from the particle source from a divergent state to a convergent state.

In some of these embodiments, the pre-accelerator system includes an electrostatic lens configured to transition the particle beam from the particle source from a divergent state to a convergent state. In some of these embodiments, the electrostatic lens is controllable to tune beam focus or backflow defocus.

In some of these embodiments, the pre-accelerator system includes a magnetic focusing device controllable to tune beam focus or backflow defocus.

In some of these embodiments, the pre-accelerator system includes a pre-accelerator tube controllable to tune beam focus or backflow defocus.

In some of these embodiments, the beam system includes a plurality of power supplies configured to adjustably output a variable power to the magnetic focusing device, the electrostatic lens, and the pre-accelerator tube.

In some of these embodiments, the beam system is configured to accelerate the charged particles to their maximum cross section before entrance into the accelerator. In some of these embodiments, the charged particles are negative hydrogen ions. In some of these embodiments, the beam system is configured to accelerate the charged particles to an energy of 100 keV before entrance into the accelerator. In some of these embodiments, the beam system is configured to accelerate the charged particles to their maximum cross section at a position in a pre-accelerator tube of the pre-accelerator system. In some of these embodiments, the position is in a central region of the pre-accelerator tube.

In some of these embodiments, the beam system includes a vacuum pump chamber configured to remove gas exiting the accelerator into the pre-accelerator system.

In some of these embodiments, the particle source is positioned such that the charged particle beam is emitted along a same or substantially similar axis that traverses the accelerator, along which charged particles passing through the accelerator are accelerated.

In some of these embodiments, the beam system includes a control system. In some of these embodiments, the control system is configured to receive operating parameters or instructions from a computing device. In some of these embodiments, the control system is configured to transmit operating data to the computing device. In some of these embodiments, the control system is configured to control at least one of the following: a voltage applied to an electrode of the particle source, a voltage applied to an electrostatic lens of the pre-accelerator system, a voltage applied to a pre-accelerator device of the pre-accelerator system, a voltage applied to a magnetic focusing device of the pre-accelerator system, a voltage applied to the accelerator, a voltage output by a power supply of the beam system, adjustment of beam position for alignment, adjustment of beam focal position, or adjustment of backflow defocus amount.

In some of these embodiments, the beam system is configured for use in Boron Neutron Capture Therapy (BNCT).

In many embodiments, a method of operating a beam system includes emitting a beam comprising charged particles from a particle source, accelerating the beam with a pre-accelerator system towards an accelerator, and accelerating the beam with the accelerator.

In some of these embodiments, the pre-accelerator system includes one or more of: an electrostatic lens, a pre-accelerator device, or a magnetic focusing device. In some of these embodiments, the electrostatic lens is an einzel lens, the pre-accelerator device is a pre-accelerator tube including a plurality of acceleration terminals, and the magnetic focusing device is a solenoid.

In some of these embodiments, the accelerator is a tandem accelerator. In some of these embodiments, the tandem accelerator includes a charge exchange device. In some of these embodiments, accelerating the beam with the pre-accelerator system towards the accelerator includes accelerating the beam such that the charged particles reach their maximum cross section prior to entering the accelerator. In some of these embodiments, the charged particles are negative hydrogen ions. In some of these embodiments, the charged particles reach their maximum cross-section within a pre-accelerator tube of the pre-accelerator system.

In some of these embodiments, the method includes converging the beam with the pre-accelerator system.

In some of these embodiments, the method includes adjusting power supplied to the pre-accelerator system to control convergence of the beam. In some of these embodiments, converging the beam further comprises transitioning the beam from a divergent state to a convergent state with the pre-accelerator system. In some of these embodiments, the beam is converged with one or more of: an electrostatic lens, a pre-accelerator device, or a magnetic focusing device. In some of these embodiments, the pre-accelerator system includes an electrostatic lens, a pre-accelerator device, and a magnetic focusing device. In some of these embodiments, the electrostatic lens is downstream of the particle source, the pre-accelerator device is downstream of the electrostatic lens, and the magnetic focusing device is downstream of the pre-accelerator device.

In some of these embodiments, the method includes adjusting power supplied to the pre-accelerator device to control convergence of the beam.

In some of these embodiments, the method includes adjusting power supplied to the magnetic focusing device to control focus of the beam.

In some of these embodiments, the method includes adjusting power supplied to the pre-accelerator device to control convergence of the beam and adjusting power supplied to the magnetic focusing device to control focus of the beam. In some of these embodiments, adjusting power supplied to the magnetic focusing device to control focus of the beam includes adjusting power supplied to the magnetic focusing device to focus the beam at an input aperture of the accelerator.

In some of these embodiments, the particle source is positioned such that the beam is emitted along a same or substantially similar axis that traverses the accelerator, along which charged particles passing through the accelerator are accelerated.

In some of these embodiments, the particle source is one of a volume type source and a surface type source.

In some of these embodiments, the method includes defocusing backflow from the accelerator with the pre-accelerator system. In some of these embodiments, the backflow includes ionized background gas. In some of these embodiments, the method includes adjusting power supplied to the pre-accelerator system to control defocusing of the backflow. In some of these embodiments, the method includes adjusting power supplied to the pre-accelerator system to cause backflow to be collected by one or more components of the beam system. In some of these embodiments, the method includes adjusting power supplied to the pre-accelerator system to cause backflow to avoid a backflow sensitive component of the particle source. In some of these embodiments, the backflow sensitive component is a filament.

In some of these embodiments, the backflow is defocused with one or more of: an electrostatic lens, a pre-accelerator device, or a magnetic focusing device.

In some of these embodiments, the pre-accelerator system includes an electrostatic lens, a pre-accelerator device, and a magnetic focusing device. In some of these embodiments, with respect to travel of the beam, the electrostatic lens is downstream of the particle source, the pre-accelerator device is downstream of the electrostatic lens, and the magnetic focusing device is downstream of the pre-accelerator device. In some of these embodiments, the method includes adjusting power supplied to the pre-accelerator device to control defocusing of the backflow. In some of these embodiments, the method includes adjusting power supplied to the magnetic focusing device to control defocusing of the backflow. In some of these embodiments, the method includes adjusting power supplied to the pre-accelerator device to control defocusing of the backflow and adjusting power supplied to the magnetic focusing device to control defocusing of the backflow.

In some of these embodiments, the particle source is positioned such that the beam is emitted along a same or substantially similar axis that traverses the accelerator, along which charged particles passing through the accelerator are accelerated.

In some of these embodiments, the method includes performing vacuum removal of gas. In some of these embodiments, the method includes performing vacuum removal of gas at a first position between the pre-accelerator system and the accelerator and at a second position between the particle source and the pre-accelerator system. In some of these embodiments, accelerating the beam with the pre-accelerator system towards the accelerator includes accelerating the beam such that the charged particles reach their maximum cross section prior to entering the accelerator.

In some of these embodiments, the method includes controlling, with a control system of the beam system, at least one of the following: a voltage applied to an electrode of the particle source, a voltage applied to an electrostatic lens of the pre-accelerator system, a voltage applied to a pre-accelerator device of the pre-accelerator system, a voltage applied to a magnetic focusing device of the pre-accelerator system, a voltage applied to the accelerator, a voltage output by a power supply of the beam system, adjustment of beam position for alignment, adjustment of beam focal position, or adjustment of backflow defocus amount.

In some of these embodiments, the method includes one or more of receiving, using a control system, operating parameters or instructions from a computing device, or transmitting, using the control system, operating data to the computing device. In some of these embodiments, the control system is configured for one or more of wireless or wired communications.

In some of these embodiments, the method includes applying the beam to a target. In some of these embodiments, the particle source is an ion source and the charged particles are negative hydrogen ions. In some of these embodiments, the method includes converting the beam from a negative hydrogen ion beam to a proton beam in the accelerator. In some of these embodiments, applying the beam to a target includes applying the proton beam to a neutron generating target.

In some of these embodiments, the method includes using the beam system in Boron Neutron Capture Therapy (BNCT).

In many embodiments, a method of defocusing backflow in a beam system includes vacuuming gaseous neutrals from a tandem accelerator and biasing a pre-accelerator system coupled to the tandem accelerator. In some of these embodiments, the pre-accelerator system is configured to defocus positive ionized gas that is accelerated by a magnetic field in an opposite direction of an accelerated beam of the beam system. In some of these embodiments, the pre-accelerator system includes one or more of a pre-accelerator tube, an einzel lens, a magnetic focusing device, or solenoid.

In some of these embodiments, the method includes electrically coupling the pre-accelerator tube at a first pre-accelerator tube terminal with a first power supply and at a second pre-accelerator tube terminal with ground.

In some of these embodiments, the pre-accelerator system is positioned adjacent to and downstream from an ion source.

In some of these embodiments, the pre-accelerator tube is mounted adjacent to and downstream from the einzel lens.

In some of these embodiments, the magnetic focusing device is mounted adjacent to and downstream from the pre-accelerator tube.

In some of these embodiments, the pre-accelerator tube is positioned downstream from one or more of an einzel lens or an ion source.

In some of these embodiments, the einzel lens is positioned downstream from an ion source.

In some of these embodiments, the magnetic focusing device is positioned downstream from one or more of an einzel lens, the pre-accelerator tube, or an ion source.

In some of these embodiments, a first vacuum pump chamber is positioned between the pre-accelerator system and the tandem accelerator. In some of these embodiments, a second vacuum pump chamber is positioned between the ion source and the pre-accelerator system.

In some of these embodiments, one or more vacuum pump chambers are positioned on a top surface of the tandem accelerator.

In some of these embodiments, the method includes cooling, using a first cooling device, a backplate of the ion source. In some of these embodiments, the backplate includes one or more filaments. In some of these embodiments, the method includes cooling, using a second cooling device, the einzel lens. In some of these embodiments, one or more of the first cooling device or second cooling device includes water cooling.

In some of these embodiments, the method includes biasing the magnetic focusing device using a first power supply to tune beam focusing or backflow defocusing properties of the magnetic focusing device.

In some of these embodiments, the method includes biasing the einzel lens using a second power supply to tune beam focusing or backflow defocusing properties of the einzel lens.

In some of these embodiments, the method includes biasing the pre-accelerator tube using a third power supply to tune beam focusing or backflow defocusing properties of the pre-accelerator tube.

In some of these embodiments, the method includes positioning the ion source such that the ions are emitted along a same or substantially similar axis that traverses the tandem accelerator, along which ions passing through the tandem accelerator are accelerated.

In some of these embodiments, the method includes one or more of receiving, using a control system, operating parameters or instructions from a computing device, or transmitting, using the control system, operating data to the computing device.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

As used herein and in the appended claims, the singular forms "a," "an," and "the" include plural referents unless the context clearly dictates otherwise.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. A beam system, comprising:
   a particle source configured to emit a charged particle beam;
   a pre-accelerator system configured to accelerate the charged particle beam from the particle source;
   an accelerator configured to accelerate the charged particle beam from the pre-accelerator system;
   a first vacuum pump chamber positioned between the pre-accelerator system and the accelerator, wherein the first vacuum pump chamber is configured to remove gas exiting the accelerator into the pre-accelerator system; and
   a second vacuum pump chamber positioned between the particle source and the pre-accelerator system.

2. The beam system of claim 1, wherein the second vacuum pump chamber is configured to remove gas exiting the pre-accelerator system into the particle source.

3. The beam system of claim 1, wherein the first vacuum pump chamber and the second vacuum pump chamber are positioned on a same side of the beam system.

4. The beam system of claim 1, wherein the accelerator is a tandem accelerator.

5. The beam system of claim 1, wherein the particle source is an ion source.

6. The beam system of claim 1, further comprising a control system.

7. The beam system of claim 6, wherein the control system is configured to control at least one of the following: a voltage applied to an electrode of the particle source, a voltage applied to a pre-accelerator device of the pre-accelerator system, a voltage applied to a magnetic focusing device of the pre-accelerator system, a voltage applied to the accelerator, a voltage output by a power supply of the beam system, an alignment of a beam position, a beam focal position, or backflow defocusing.

8. The beam system of claim 1, configured for use in Boron Neutron Capture Therapy (BNCT) and further comprising:
   a high energy beam line extending from the accelerator to a lithium target configured to generate neutrons.

9. The beam system of claim 1, wherein the charged particle beam is an ion beam comprising negative hydrogen ions.

10. The beam system of claim 1, wherein the beam system is configured to accelerate charged particles of the charged particle beam to their maximum cross section before entrance into the accelerator.

11. The beam system of claim 10, wherein a position at which the maximum cross section is reached is in a pre-accelerator tube of the pre-accelerator system.

12. The beam system of claim 11, wherein the position is in a central region of the pre-accelerator tube.

13. The beam system of claim 10, wherein the charged particles are negative hydrogen ions.

14. The beam system of claim 10, wherein the beam system is configured to accelerate the charged particles to an energy of 100 keV before entrance into the accelerator.

15. The beam system of claim 1, wherein the pre-accelerator system is configured to cause the charged particle beam to propagate from the particle source to converge at an input aperture of the accelerator.

16. The beam system of claim 1, wherein the pre-accelerator system is configured to defocus and collect ionized backflow that propagates from the accelerator towards the particle source.

17. A method of operating a beam system, the method comprising:
  emitting a beam comprising charged particles from a particle source;
  accelerating the beam with a pre-accelerator system towards an accelerator;
  accelerating the beam with the accelerator;
  removing gas exiting the accelerator into the pre-accelerator system using a first vacuum pump chamber; and
  removing gas exiting the pre-accelerator system into the particle source using a second vacuum pump chamber.

18. The method of claim 17, wherein the beam is directed onto a lithium target that generates neutrons.

19. A beam system, comprising:
  a particle source configured to emit a charged particle beam;
  a pre-accelerator system configured to accelerate the charged particle beam from the particle source;
  an accelerator configured to accelerate the charged particle beam from the pre-accelerator system;
  a first vacuum pump chamber positioned between the pre-accelerator system and the accelerator; and
  a second vacuum pump chamber positioned between the particle source and the pre-accelerator system, wherein the second vacuum pump chamber is configured to remove gas exiting the pre-accelerator system into the particle source.

20. The beam system of claim 18, configured for use in Boron Neutron Capture Therapy (BNCT) and further comprising: a high energy beam line extending from the accelerator to a lithium target configured to generate neutrons.

* * * * *

UNITED STATES PATENT AND TRADEMARK OFFICE
CERTIFICATE OF CORRECTION

| | | |
|---|---|---|
| PATENT NO. | : 12,070,625 B2 | Page 1 of 1 |
| APPLICATION NO. | : 17/984954 | |
| DATED | : August 27, 2024 | |
| INVENTOR(S) | : Dunaevsky et al. | |

It is certified that error appears in the above-identified patent and that said Letters Patent is hereby corrected as shown below:

In the Claims

<u>Column 26,</u>
Line 24, Claim 20, "claim 18" should read --claim 19--.

Signed and Sealed this
Fifth Day of August, 2025

Coke Morgan Stewart
*Acting Director of the United States Patent and Trademark Office*